United States Patent
Lewis et al.

(10) Patent No.: US 7,960,125 B2
(45) Date of Patent: Jun. 14, 2011

(54) IDENTIFICATION OF THYMICALLY DERIVED CD4 T CELLS BY PROTEIN TYROSINE KINASE 7 EXPRESSION

(75) Inventors: David B. Lewis, Stanford, CA (US); Christopher Haines, Menlo Park, CA (US); Thierry Giffon, Mountain View, CA (US); Xiaowei Lu, Charlottesville, VA (US); Marc Tessier-Lavigne, South San Francisco, CA (US); Douglas T. Ross, Huntsville, AL (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 435 days.

(21) Appl. No.: 12/238,288

(22) Filed: Sep. 25, 2008

(65) Prior Publication Data

US 2009/0170101 A1 Jul. 2, 2009

Related U.S. Application Data

(60) Provisional application No. 60/975,101, filed on Sep. 25, 2007.

(51) Int. Cl.
*G01N 33/53* (2006.01)

(52) U.S. Cl. .................................. 435/7.1; 435/7.24
(58) Field of Classification Search .................. None
See application file for complete search history.

(56) References Cited

OTHER PUBLICATIONS

Boursalian; et al., "Continued maturation of thymic emigrants in the periphery", Nature Immunology, Apr. 2004, 5 (4):418-25.
Chen; et al., "Impaired Allogeneic Activation and T-helper I Differentiation of Human Cord Blood Naive CD4 T Cells", Biology of Blood and Marrow Transplantation (2006), 12:160-171.
Hazenberg; et al., "Thymic output: a bad TREC record", Nature Immunology, Feb. 2003, 4(2):97-99.
Juliien; et al., "Decreased CD154 expression by neonatal CD4+ T cells is due to limitations in both proximal and distal events of T cell activation", International Immunology (2003), 15(12):1461-1472.
Lu; et al., "PTK7/CCK-4 is a novel regulator of planar cell polarity in vertebrates", Nature, Jul. 2004, 430:93-98.
McFarland; et al., "Identification of a human recent thymic emigrant phenotype", PNAS, Apr. 11, 2000, 97 (8):4215-4220.
Nanoyama; et al., "Diminished Expression of CD40 Ligand by Activated Neonatal T Cells", J. Clin. Invest., Jan. 1995, 95:66-75.

*Primary Examiner* — Zachary Skelding
(74) *Attorney, Agent, or Firm* — Bozicevic, Field & Francis LLP; Pamela J. Sherwood

(57) ABSTRACT

The invention provides methods of identifying naïve T cells by expression of PTK7.

11 Claims, 11 Drawing Sheets

SEQUENCE LISTING

<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: PCR Forward Primer

<400> SEQUENCE: 1
ccatgctgac acctctggtt                                           20

<210> SEQ ID NO 2
<211> LENGTH: 21
<212> TYPE: DNA
<213> ORGANISM: Artificial Sequence
<220> FEATURE:
<223> OTHER INFORMATION: Reverse Primer

<400> SEQUENCE: 2
tcgtcagaac ggtgaatgaa g                                         21

<210> SEQ ID NO 3
<211> LENGTH: 23
<212> TYPE: DNA
<213> ORGANISM: Artificial Sequence
<220> FEATURE:

```
<223> OTHER INFORMATION: Probe FAM-TAMRA

<400> SEQUENCE: 3
cacggtgatg cataggcacc tgc                                              23

<210> SEQ ID NO 4
<211> LENGTH: 21
<212> TYPE: DNA
<213> ORGANISM: Artificial Sequence
<220> FEATURE:
<223> OTHER INFORMATION: PCR Forward Primer

<400> SEQUENCE: 4
cctgatcctc ttgtcccaca g                                                21

<210> SEQ ID NO 5
<211> LENGTH: 26
<212> TYPE: DNA
<213> ORGANISM: Artificial Sequence
<220> FEATURE:
<223> OTHER INFORMATION: PCR Reverse Primer

<400> SEQUENCE: 5
ggatttagag tctctcagct ggtaca                                           26

<210> SEQ ID NO 6
<211> LENGTH: 22
<212> TYPE: DNA
<213> ORGANISM: Artificial Sequence
<220> FEATURE:
<223> OTHER INFORMATION: Probe FAM-TAMRA

<400> SEQUENCE: 6
atccagaacc ctgaccctgc cg                                               22

<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
atcacgagca gctggtttct                                                  20

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
ccattcctga agcaaggaaa                                                  20

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaaaacagcc tttgggacac                                                  20

<210> SEQ ID NO 10
```

```
<211> LENGTH: 20
<212> TYPE: DNA
<213> ORGANISM: Artificial Sequence
<220> FEATURE:
<223> OTHER INFORMATION: PCR Primer

<400> SEQUENCE: 10
gtgacatgga gggctgaact                                              20

<210> SEQ ID NO 11
<211> LENGTH: 32
<212> TYPE: DNA
<213> ORGANISM: Artificial Sequence
<220> FEATURE:
<223> OTHER INFORMATION: Forward PCR Primer

<400> SEQUENCE: 11
ggaattcagc caccatggga gcccgcccgc tg                                32

<210> SEQ ID NO 12
<211> LENGTH: 29
<212> TYPE: DNA
<213> ORGANISM: Artificial Sequence
<220> FEATURE:
<223> OTHER INFORMATION: Reverse PCR Primer

<400> SEQUENCE: 12
tccccgcgga cttcccgaac atctccacc                                    29

<210> SEQ ID NO 13
<211> LENGTH: 6
<212> TYPE: DNA
<213> ORGANISM: Artificial Sequence
<220> FEATURE:
<223> OTHER INFORMATION: Forward PCR Primer Kozak consensus translation
      start site ribosome binding site sequence

<400> SEQUENCE: 13 gccacc                                                             6

<210> SEQ ID NO 14
<211> LENGTH: 20
<212> TYPE: DNA
<213> ORGANISM: Artificial Sequence
<220> FEATURE:
<223> OTHER INFORMATION: Human PTK7 Forward Primer

<400> SEQUENCE: 14
ccacctacca atggttccga                                              20

<210> SEQ ID NO 15
<211> LENGTH: 21
<212> TYPE: DNA
<213> ORGANISM: Artificial Sequence
<220> FEATURE:
<223> OTHER INFORMATION: Human PTK7 Reverse Primer

<400> SEQUENCE: 15
tgctctgacc atcagaaagg g                                            21

<210> SEQ ID NO 16
<211> LENGTH: 20
<212> TYPE: DNA
<213> ORGANISM: Artificial Sequence
<220> FEATURE:
<223> OTHER INFORMATION: Mouse PTK7 Forward Primer

<400> SEQUENCE: 16
```

```
caggcattgc tgaagactgg                                               20

<210> SEQ ID NO 17
<211> LENGTH: 20
<212> TYPE: DNA
<213> ORGANISM: Artificial Sequence
<220> FEATURE:
<223> OTHER INFORMATION: Mouse PTK7 Reverse Primer

<400> SEQUENCE: 17
ggttgtggcg aagagaaacg                                               20
```

US 7,960,125 B2

IDENTIFICATION OF THYMICALLY DERIVED CD4 T CELLS BY PROTEIN TYROSINE KINASE 7 EXPRESSION

GOVERNMENT RIGHTS

This invention was made with Government support under contract NIH R21 HD-37589 awarded by the National Institute of Health. The Government has certain rights in this invention.

BACKGROUND OF THE INVENTION

T lymphocytes are cells of the adaptive immune system that mainly develop in the thymus and are selected to express a unique and exquisitely-specific T-cell receptor (TCR) that will both remain tolerant (non-responsive) to self antigens, and yet bet able to recognize and respond to a foreign linear peptide in the context of self-major histocompatibility complex (MHC) molecules.

During differentiation, progenitors to T cells arise from stem cells in the bone marrow, and are then recruited to the thymus, entering via vessels in the perimedullary cortex, where they begin differentiation into T cells. Following a series of ligand/receptor and cytokine or chemokine/receptor interactions, the initial "double negative" thymocytes progress through maturation, eventually rearranging T-cell receptor genes to generate a productive TCRβ chain gene. The TCRβ chain protein is coexpressed with the pre-T alpha receptor, and this triggers co-expression of both the CD4 and CD8 coreceptors by cells that are referred to as double positive thymocytes (DPs). Upon a productive TCRα rearrangement, the TCRβ and TCRα chain proteins are coexpressed as a heterodimer in association with proteins of the CD3 complex. Positive selection then occurs, resulting in the upregulation of the surface levels of the αβ TCR/CD3 complex and loss of either CD8 to form CD4+CD8− thymocytes (MHC class II selection), or loss of CD8 to form CD4−CD8+ thymocytes (MHC class I selection). These single-positive thymocytes move into the medulla where negative selection occurs to purge the repertoire of autoreactive T cells.

Following selection, these naïve T cells are exported from the thymus. The rate of thymic export appears to remain constant throughout the lifetime of the individual but the volume of export is proportional to the volume of residual thymic mass index. Therefore, as individuals age, their thymus involutes and is largely converted into fat, and there is a concomitant decrease in the number of recent thymic emigrants that are exported on a daily basis. Despite this reduction in thymic output throughout the time course of life in individuals, the absolute number of T cells in the peripheral T-cell pool remains surprisingly constant throughout life.

Following thymic development, $CD4^+$ and $CD8^+$ T cells are exported into the peripheral circulation as naïve T cells, which survey self-major histocompatibility complex (MHC) molecules for foreign peptide antigens. In response to cognate antigen, they differentiate into effector and memory T lymphocytes. The developmental stage of human T-cell maturation following export from the thymus has not been extensively characterized. A limited number of studies in other species have suggested that recent thymic emigrants (RTEs) are not fully mature and require a developmental period of post-thymic maturation to become fully functional T cells. In the rat, lack of both RT6 and CD45RC expression distinguish RTEs from the rest of the mature T cell pool. Unfortunately, human homologs for markers such as RT6 or CD45RC have not been identified for humans, and experimental approaches useful in animals, such as ectopic GFP expression or intrathymic injections of dyes, are not possible. Therefore, aspects of human post-thymic T cell development remain unknown.

In order to overcome these challenges, investigators have developed a surrogate marker for RTE frequency in human T cell populations called sjTREC content analysis. sjTRECs, or signal joint T-cell receptor excision circles, are the signal joint byproducts of VDJ recombination leftover following TCR rearrangement in the thymus. Because they lack an origin of replication, they are not replicated during each cell division, and as such are diluted in T cells following cell proliferation. Relative or absolute TREC content can be used to determine the relative "age" of bulk populations of cells, and to roughly estimate the contribution of thymic output to the T-cell pool. However, TRECs can only be detected with a PCR assay that requires killing the cells; the TREC assay cannot determine at a single cell level whether a T cell is an RTE; and because a TREC has to be split between two daughter cells, even $TREC^+$ naïve T cells may have undergone some rounds of division. TRECs are also assumed to be equally stable in various naïve T-cell populations in the absence of cell proliferation, but whether this is actually the case remains unknown.

A unique cell-surface marker that directly detects naïve T cells, particularly live RTEs, at the single cell level is highly desirable for enumerating these cells and understanding their function. The ready identification of these cells in humans and an understanding of their maturation and functional attributes are important not only for understanding the basic biology of T-cell development and function, but also for the development of better vaccines for human neonates and infants. Furthermore, such a marker would allow one to monitor the kinetics of thymic output in normal patients over the adult lifespan, and T-cell reconstitution in those patients with transient deficiencies in CD4+ T cells, such as those with HIV-infection, hematopoietic stem cell transplantation, or chemotherapy treatment, and those with inherited immunodeficiencies involving T cells, such as severe combined immunodeficiency (SCID).

BRIEF SUMMARY OF THE INVENTION

Methods are provided for the detection, identification and isolation of naïve T cells. It is shown herein that thymocytes and naïve T cells, e.g. recent thymic emigrants, express on their cell surface protein tyrosine kinase 7 (PTK7), a member of the receptor tyrosine kinase family. The four major subpopulations of murine and human thymocytes express PTK7 mRNA and protein, which decreases with maturation. A discrete subset of human peripheral naïve T cells express PTK7. The detection of RTE cells in the peripheral blood provides a sensitive method for assessment of thymic function, and finds use in monitoring the status of individuals undergoing chemotherapy; treatment for HIV infection; and other chronic or acute conditions affecting the generation of naïve T cells. The detection of RTE cells in the peripheral blood also provides a sensitive s method of monitoring the status of patients treated to improve immune function, e.g. following hematopoietic stem cell transplantation, cytokine immunotherapy, etc.

In some embodiments, the invention provides methods of determining whether a T cell in a biological sample is a naïve T cell by detecting the cell surface antigen PTK7. In other embodiments, the invention provides methods of identifying naive T cells by identifying $PTK7^+$ T cells according to their level of expression of the PTK7 biomarkers in a biological sample. In some embodiments, the T cells are $CD4^+$ T cells. In other embodiments, the T cells are $CD8^+$ T cells. Such cells may be further classified as recent thymic emigrants. Human cells are of particular interest, as are CD4+ cells. A biological sample of particular interest is peripheral blood.

In another embodiment, the presence of naïve T cells in a biological sample is determined by quantitating the level of PTK7 in the sample. Any convenient method may be used for the quantitation of PTK7, including detection of the protein by immunoassay, e.g. ELISA, immunohistochemistry, flow cytometry, etc.; detection of PTK7 mRNA, etc.

In other embodiments, the invention provides methods of making an isolated population of naive T-cells, which may be CD4+ T cells, and which may further be RTE T cells. In one embodiment, the population is isolated by obtaining a biological sample comprising T-cells and determining the level of expression of PTK7 on the surface of the T-cells and isolating the PTK7+ T-cells from those T-cells which are PTK7−. The cells may be further separated on the basis of CD4 and/or the CD8 expression.

In another embodiment, the invention provides kits comprising materials specifically useful in performing the above methods. A kit for identifying or isolating a naive T-cell population, for example, can comprise an antibody that binds PTK7. The label is preferably labeled (e.g., a fluorescent, magnetic or isotopically label). In addition, the kit may further provide instructions for formulating the T-cell population in a suitable media for contacting with cells in vivo or in vitro.

In another aspect, the invention provides methods for identifying immunosuppressive, particularly thymus-damaging drugs by determining their effect on PTK7+ cells, e.g. PTK+ cells in the peripheral blood. As PTK7+ cells are typically recent thymic emigrants, such detection provides a sensitive means of monitoring thymic function.

In another aspect, the invention provides methods for assessing the immunostimulatory impact on thymic function of drugs, such as the cytokines IL-2, IL-7, or TSLP, by determining the levels of PTK7+ cells in the peripheral blood before and after treatment intervention.

In another aspect, the invention provides a means to isolate RTEs by means of antibody staining of surface PTK7, and using these cells as a means of adoptive immunotherapy, such as in settings of T-cell lymphopenia.

In another aspect, the invention provides a means to screen blood samples in newborns for severe inherited T-cell immunodeficiency, such as severe combined immunodeficiency, by analyzing blood spots for PTK7 protein.

DETAILED DESCRIPTION OF THE INVENTION

Definitions

Figure 1:
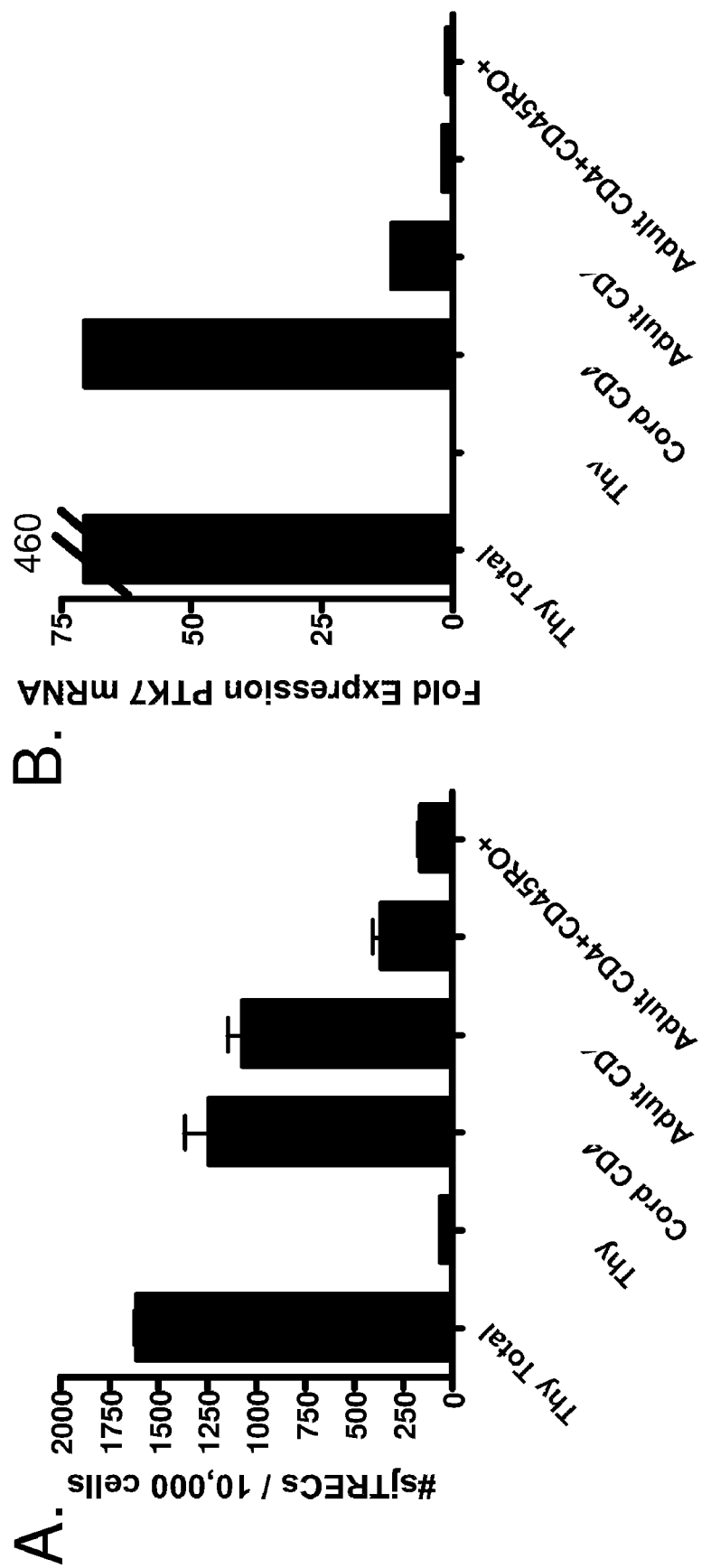
FIG. 1. Human CD4+CD8− thymocytes and cord blood (neonatal) CD4+CD45RA$^{hi}$ peripheral T cells (which are enriched in RTEs) contain higher levels of TRECs and higher levels of PTK7 transcripts than adult naïve CD4+CD45RA$^{hi}$ T cells. (A). Cells were either fluorescent activated cell sorter (FACS)-purified or magnetic activated cell sorter (MACS)-purified to >90% purity, then total DNA was extracted, and a real-time PCR based assay for detecting sjTRECs was performed, after normalization for cell number based on real-time PCR detection of a conserved TCR alpha genomic sequence. (B). A separate aliquot of the same populations of cells was used for RNA extraction, then 250 ng was used to make cDNA using reverse transcriptase and random hexamers, and the cDNA was used in a real-time PCR based assay for detecting PTK7 transcripts. 18S rRNA serves as a normalization control between samples for cell number. A separate cDNA production reaction with 250 ng of RNA and no reverse transcriptase added was used as a negative control for amplification from genomic DNA, and there was >5 Ct difference (minimal amplification) of 18S rRNA under this condition.

Unless otherwise stated, the following terms used in the specification and claims have the meanings given below.

It is noted here that as used in this specification and the appended claims, the singular forms "a," "an," and "the" include plural reference unless the context clearly dictates otherwise.

By a "population of cells" is meant a plurality of cells, preferably at least $10^3$, $10^4$, $10^5$, $10^6$, $10^7$, $10^8$, $10^9$, $10^{10}$, or $10^{11}$ cells. The population in some embodiments has from $10^5$ to $10^7$ cells, $10^6$ to $10^8$ cells, or from $10^8$ to $10^{11}$ cells, or $10^{10}$ to $10^{12}$ cells.

Immune conditions, diseases, disorders and reactions or responses to be monitored or treated according to the methods and compositions of the invention means a disease in which the immune system contributes to pathogenesis. Of interest are immune conditions where there is a deficiency in the generation of T cells, particularly relating to thymic maturation of T cells. Thymic activity is compromised by certain viral infections, including HIV infection, by immunosuppressive drugs including chemotherapy, by inborn errors of metabolism and other genetic defects, thymectomy, and the like. Also of interest are treatments to restore immune function, e.g., hematopoietic stem cell or thymus transplantation or cytokines, such as IL-2, IL-7, and TSLP.

The response of a patient to treatment may be monitored by determining the frequency of naïve, particularly RTE, T cells in a sample from a patient. A decrease in the number of naïve, or RTE, T cells in the sample may be used as an indication to decrease immunosuppressive treatment. An increase in RTEs in a sample may be used as an indication to reduce immunostimulatory treatment, such as with cytokines.

"Recent thymic emigrant" refers to a T cell in tissues other than the thymus, which T cells are typically antigenically naïve, that is they have not yet been stimulated by an antigen presenting cell in an MHC+foreign peptide antigen context. A naïve T cell may be defined as a recent thymic emigrant when it has emigrated from the thymus not more than 6 months earlier, not more than 4 months earlier, not more than 2 months earlier, not more than 1 month earlier, or less. In some embodiments of the invention an RTE may have emigrated from the thymus not more than 2 months earlier.

"CD," "cluster of differentiation" or "common determinant" as used herein refers to cell surface molecules recognized by antibodies. Expression of some CDs (e.g., CD4, CD8) is specific for cells of a particular lineage or maturational pathway, and the expression of others varies according to the state of activation, position, or differentiation of the same cells. Preferably, in some embodiments, the CD determinants are human when the isolated cells are to be administered to a human or a human immune response is being studied.

As used herein, the term PTK7 refers to the "protein tyrosine kinase 7" protein, which as shown herein is present on thymically derived naïve T cells. The PTK7 protein is described in the literature. The gene for human protein tyrosine kinase 7 (PTK7), which is also called CCK-4 or colon carcinoma kinase-4, was originally cloned in 1995 by Mossie's group in an effort to identify novel proteins involved in colon tumorigenesis (see Mossie et al. (1995) *Oncogene* 11: 2179-2184; and Park et al. (1996) *J. Biochem.* 119: 235-239, each herein specifically incorporated by reference). PTK7 shares similarities with other PTK family members, but it contains several key mutations in conserved regions that prevent it from being an active kinase, including the DFG motif, the GxGxxG region, and the HRDL domain. Many of these residues are crucial for ATP binding in the cytoplasmic domain so that it is predicted to be a "dead" kinase. The protein structure contains 7 Ig-like domains in the extracellular portion, a conserved ~20 amino acid single pass transmembrane region, and a ~300 amino acid cytoplasmic region that contains many N-glycosylation sites and 6 tyrosines.

The term "PTK7$^+$" refers to cells which stain when treated with a labeled antibody directed toward PTK7. Generally, cells are distinguished according to their PTK7 expression levels based upon readily discernible differences in staining intensity as is known to one of ordinary skill in the art. In some embodiments, the cut off for designating a cell as a PTK7$^{+-}$ cell can be set in terms of the fluorescent intensity distribution observed for the cells as compared to an isotype-matched control. A PTK7$^-$ cell can be designated as one which does not stain any more brightly than the staining with an isotype matched control. The designation of a cell type with respect to its levels of expression of a recited biomarker or CD is meant to describe the cell being referenced by its biomarker expression phenotype and is not necessarily an indicator that expression levels were actually determined for the referenced cell.

PTK7$^+$ naive T-cell populations for use according to the invention are cell populations which have been positively selected for the PTK7 biomarker. In some embodiments, the cells have been further characterized with respect to other CD determinants, particularly the CD4 determinants (e.g., positively or negatively selected for with respect to CD4). In other embodiments, the cells have been further characterized according to their expression of common determinants other than CD4, including CD3, and CD8, where the PTK7 cells may be CD3$^+$ T cells, or CD8$^+$ T cells. In preferred embodiments, the cell populations are substantially the selected cell type.

As used herein, the term "CD4" refers to a cell-surface glycoprotein typically found on the mature helper T cells and immature thymocytes, as well as on monocytes and macrophages. On T cells, CD4 is the co-receptor for the T cell receptor (TCR) and recruits the tyrosine kinase lck. With its D1-portion, CD4 can attach to the β2-domain of MHC class II molecules. CD4$^+$ refers to cells which stain brightly when contacted with labeled anti-CD4 antibody, and CD4$^-$ refers to cells of a type which stain the least brightly, dull or not at all, when contacted with a fluorescently labeled CD4 antibody. Generally, the cells are distinguished according to their CD4 expression levels based upon a readily discernible differences in staining intensity as the CD4 staining is clearly bimodal. In some embodiments, the frequency distribution of the CD4 staining is obtained for all the cells and the population curve fit to a higher staining and lower staining population, and cells assigned to the population to which they most statistically are likely to belong in view of a statistical analysis of the respective population distributions. In some embodiments, the CD4$^-$ cells stain two to three fold less intensely than the CD4$^+$ cells. Particularly preferred methods are also exemplified in the Examples.

Methods of segregating CD4 T cells into + and – categories are known to persons of ordinary skill in the art. In some embodiments, the frequency distribution of the CD4 staining is obtained for all the cells and the population curve fit to a higher staining and lower staining population, and cells assigned to the population to which they most statistically are likely to belong in view of a statistical analysis of the respective population distributions. In some embodiments, the CD4$^+$ cells stain two- to three-fold more intensely than the CD4$^-$ cells.

As used herein, the term "sample" or "biological sample" refers to tissues or body fluids removed from a mammal, preferably human, and which contain naive T cells, including, but not limited to, PTK7$^+$ T-cells. In some embodiments, the samples are taken from individuals with an immune response which needs to be monitored. In some embodiments, the individual has an immunodeficiency. In some embodiments, the individual is being treated with an agent that is immunosuppressive, e.g. a chemotherapeutic agent. In other embodiments the individual is being treated with an agent that restores immune function, e.g. anti-viral therapy such as HAART; stem or progenitor cell replacement, thymus transplant, or immunostimulatory drugs, e.g., cytokines. Samples preferably are blood and blood fractions, including peripheral blood. The biological sample is drawn from the body of a mammal, such as a human, and may be blood, cord blood, or similar tissues or cells. Methods for obtaining such samples are well known to workers in the fields of cellular immunology and surgery. They include sampling blood in well known ways, or obtaining biopsies from the thymus or other tissue or organ.

The term "isolated" with regard to a population of cells as used herein refers to a cell population which either has no naturally-occurring counterpart or has been separated or purified from other components, including other cell types, which naturally accompany it, e.g., in normal or diseased tissues such as lung, kidney, or placenta, tumor tissue such as colon cancer tissue, or body fluids such as blood, serum, or urine. Typically, an isolated cell population is at least two-fold, four-fold, or eight-fold enriched for a specified cell type when compared to the natural source from which the population was obtained.

A population or subpopulation of cells which is "substantially" of a specified cell type is one which has a count of the specified cell type which is at least 50%, 75%, 80%, 90%, 95% or, most preferably, 98% or 99% of the total cell count of the population or subpopulation or one which is at least two-fold, four-fold, eight-fold, ten-fold or 20-fold enriched for a specified cell type as compared to a source population of the specified cell type. A substantially pure population may be at least about 50% PTK7$^+$ T cells in the population, at least about 75% PTK7$^+$ T cells in the population, at least about 80% PTK7$^+$ T cells in the population, at least about 90% PTK7$^+$ T cells in the population, or more. The term T cells as used herein refers to cells having a functional rearranged T cell receptor, which cells may be characterized as expressing CD3.

An "anti-X antibody" or "X antibody" according to the invention is an antibody which can specifically bind to X. For instance, the anti-PTK7 antibody or PTK7 antibody is capable of binding PTK7. The antibodies for use according to the invention include, but are not limited to, recombinant antibodies, polyclonal antibodies, monoclonal antibodies, chimeric antibodies, human monoclonal antibodies, humanized or primatized monoclonal antibodies, and antibody fragments. A great many lymphocyte biomarker specific antibodies are commercially available.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules.

Preferably a "label" or a "detectable moiety" is covalently or noncovalently attached to the antibody. A label may be detectable by spectroscopic, photochemical, biochemical, immunochemical, chemical, or other physical means. Particularly useful labels are fluorescent dyes. Methods of attaching labels to antibodies are well known to those of ordinary skill in the art. Particularly preferred labels are those which are attached to the antibody by a linker which can be readily cleaved or separated or subject to hydrolysis by contact with a predetermined enzyme under physiological conditions. The antibody may also be conjugated with a magnetic particle, such as a paramagnetic microbead (Miltenyi Biotec, Germany). An activated T cell bound by a magnetically labeled antibody may be isolated using techniques including, but not limited to, magnetic cell sorting. Suitably labeled antibodies to PTK7, CD4, CD8, CD3, as well as many other CDs, are commercially available and known to one of ordinary skill in the art. The antibody may be labeled before or after contact with the sample or before or after contact with the CD. The CD antibody may be labeled by contacting with a labeled antibody which binds to the CD-antibody.

Immunologic detection. As used herein the term refers to detecting, particularly to quantitating, the number of protein molecules of interest in a sample, or of cells comprising a protein of interest in a sample, by specific binding of the protein to an antibody or fragment thereof. Methods of immunologic detection are known in the art, and include, for example, "bulk" assays that utilize a cell lysate, e.g. RIA, ELISA, and various sandwich assay formats. Other methods of immunologic detection are cell specific, e.g. immunohistochemistry, cell staining and FACS analysis, and the like.

As an alternative to immunologic detection, certain methods of the invention may utilize nucleic acid detection, particularly detection of specific mRNA, in any convenient hybridization format. Such methods may be used to quantitate the presence of PTK7 specific expression in a sample at the mRNA level.

Embodiments

Methods are provided for the detection, identification and isolation of naïve T cells by determining the expression of PTK7. PTK7$^+$ T cells are shown herein to be naïve T cells, and are found in peripheral blood samples from pre-natal, neonate, to adult samples. Expression is particularly high in young individuals, e.g. neonates, but can be clearly detected at all ages. The PTK7+ naïve T cells are usually recent thymic emigrants, particularly in post-natal individuals, e.g. children older than neonates, adults, elderly, etc. The naïve T cells also express various markers for T cells, including a rearranged T cell antigen receptor, e.g. an α/β T cell antigen receptor; CD3, CD4 or CD8, etc., and in some embodiments the sample is also analyzed for expression of a T cell marker. The analysis will include suitable controls against which the expression of a test sample is compared, e.g. positive controls, negative controls, including isotype matched antibody staining for immunologic detection, and the like as known in the art.

It is a feature of the invention that naïve T cells can be identified in peripheral blood samples with a single marker, i.e. with expression of PTK7. Samples may be gated by size and scatter for lymphocytes.

For many embodiments, PTK7 is detected in peripheral blood samples, although for some purposes thymocytes samples, or other sources of lymphocytes may be used. The sample is obtained from any mammalian species, e.g. equine, bovine, porcine, canine, feline, rodent, e.g. mice, rats, hamster, primate, etc., particularly human. The sample may be obtained from a live donor, or freshly frozen tissue, a dried blood sample, tissue frozen within about 12 hours of death and maintained at below about −20° C., usually at about liquid nitrogen temperature (−180° C.) indefinitely, or maybe a lysed cell sample, e.g. a Guthrie card blood sample from a neonate.

In some embodiments the individual from which the sample is obtained has or is suspected of having an immune dysfunction, particularly an immune dysfunction affecting thymic function, for which monitoring of naïve T cell generation is of interest. Such individuals include those being screened for immune dysfunction, e.g. neonatal screening for immunodeficiency; for early detection of immune dysfunction in HIV+ individuals; for early detection of thymic damage related to chemotherapy, and the like. Such individuals also include those having a known immune dysfunction, where monitoring of thymic activity is of interest, e.g. during stem cell reconstitution, during treatment with cytotoxic and/or immunosuppressive agents, during treatment of HIV infection, and the like. In other aspects the invention provides analysis of individuals receiving immune stimulatory therapy.

Where the analysis is based on a dried or lysate sample, e.g. a cord blood lysate, biopsy sample lysate, peripheral blood lysate, etc. detection of PTK7 expression may utilize various means of determining the expression of PTK7, including immunologic and nucleic acid detection methods. In some embodiments, the presence of mRNA encoding PTK7 in a sample is detected.

Any suitable qualitative or quantitative methods known in the art for detecting specific mRNAs can be used. mRNA can be detected by, for example, hybridization to a blot or array, in situ hybridization in tissue sections, by reverse transcriptase-PCR, or in Northern blots containing poly $A^+$ mRNA. One of skill in the art can readily use these methods to determine the presence of a specific mRNA transcript in a sample. Methods of detecting specific transcripts include serial analysis of gene expression (SAGE) methodology (Velculescu et al., *Science* (1995) 270:484); differential display (DD) methodology as set forth, for example in U.S. Pat. No. 5,776,683; and U.S. Pat. No. 5,807,680; and hybridization analysis.

Hybridization analysis is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of samples by using, for example, array-based technologies having high density formats, including filters, microscope slides, or microchips, or solution-based technologies that use spectroscopic analysis (e.g., mass spectrometry).

In other screening methods utilizing cell lysates, the test sample is assayed for the presence of PTK7 polypeptide. In general, antibodies that specifically bind PTK7 are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.) The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

In some embodiments, the invention provides methods of determining whether a T-cell in a biological sample is a naïve T cell by detecting the cell surface antigen PTK7. In other embodiments, the invention provides methods of identifying naïve T-cells by identifying $PTK7^+$ T cells according to their level of expression of the PTK7 biomarkers in a biological sample. In some embodiments, the T cells are $CD4^+$ T cells. In other embodiments, the T cells are $CD8^+$ T cells, e.g. naïve T cells from neonates or infants. Such cells may be further classified as recent thymic emigrants. Human cells are of particular interest, as are $CD4^+$ cells. A biological sample of particular interest is peripheral blood. In another embodiment, the presence of naïve T cells in a biological sample is determined by quantitating the level of PTK7 in the sample.

Where the analysis is based on an intact, e.g. a viable, cell sample the detection of PTK7 expression is usually based on immunologic detection, e.g. flow cytometry, immunohistochemistry, etc. Such analysis may also be used in isolation of viable PTK7+ naïve T cells, which cells find use in experimental and therapeutic methods. The cell sample is typically prepared as a suspension in a suitable buffer, generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Detection or separation of the subject cell population will typically use immunologic specificity for detection or separation. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, eg. plate, or other convenient technique.

Of particular interest is the use of antibodies as affinity reagents. Antibodies may be monoclonal or polyclonal, and may be produced by transgenic animals, immunized animals, immortalized human or animal B-cells, cells transfected with DNA vectors encoding the antibody or T cell receptor, etc. Conveniently, these antibodies are conjugated with a label for use in detection or separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

Methods of sorting cells are well known to persons of ordinary skill in the art. Cell sorters generally are capable of separating a complex mixture of cells into fractions of a single cell type. Typically, the cells to be sorted are introduced as a thin jet of carrier liquid emanating from a small nozzle orifice. Shortly after leaving the nozzle, the fluid passes through the waist of one or more tightly focused laser beams. The scattered and fluorescence light from these interactions can be collected and analyzed to determine if there are events (e.g., the presence of a fluorescence signal indicating that a fluorophore-labeled monoclonal antibody is bound to the surface of a cell) that prompt the sorting of the cell by various means. More than one label can be monitored at a time. FACS (fluorescence activated cell sorters) can easily analyze cells at speeds greater than 200,000 events per second. Generally, the physics of the carrier fluid, however, and the statistics of distributing the cells among the droplets limits sort rates to about 50,000 cells per second. This combination of speed and reliable separation allows individual cells to be isolated for other uses.

Magnetic cell sorting may be performed using super-paramagnetic microbeads composed of iron oxide and a polysaccharide coat. Preferably the microbeads may be approximately 50 nanometers in diameter, and have a volume about one-millionth that of a typical mammalian cell. The microbeads are preferably small enough to remain in colloidal suspension, which permits rapid, efficient binding to cell surface antigens. The microbeads preferably do not interfere with flow cytometry, are biodegradable, and have negligible effects on cellular functions. The antibody coupling to the microbeads may be direct or indirect, via a second antibody to a ligand such as fluorescein.

The labeled cells are then separated as to the expression of cell surface markers as previously described, where an initial population may be limited to cells that are PTK7+. Optionally the cell population is then divided into subsets based on expression of CD3, CD4, and or CD8.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

The invention also provides compositions comprising a population of cells wherein at least 50% of said cells of said composition are naive, PTK7$^+$ T cells. The percentage of naïve T cells in the composition can be ascertained using the methodology described herein. Preferably, at least 75%, 85%, 90%, 95%, or 98% of said cells of the composition are naive T cells.

In some embodiments, the invention further provides an isolated population of naive T cells that are substantially CD4$^+$ and PTK7$^+$ or PTK7$^+$ and CD8$^+$. In some further embodiments, the isolated population is obtained by contacting a peripheral blood sample with a labeled antibody specific for the CD4 biomarker and with a labeled antibody specific for the PTK7 biomarker to identify naive cells which are CD4$^+$ and PTK7$^+$ and isolating the identified cells. In some embodiments, the CD4 antibody and the PTK7 antibody are each labeled with a different label. In further such embodiments, the CD4 antibody label and the PTK7 antibody label are each a fluorescent label. The CD4$^+$ and PTK7$^+$ cells may be identified and isolated in a fluorescent-activated cell sorter.

The cells may be administered for therapeutic purposes in any physiologically acceptable medium, normally intravascularly, although they may also be introduced into bone or other convenient site, where the cells may find an appropriate site for activation and differentiation. Usually, at least $1 \times 10^5$ cells will be administered, preferably $1 \times 10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with progenitor cell proliferation and differentiation.

The subject cells are useful for in vitro assays and screening to detect factors that are active on naïve T cells. Of particular interest are screening assays for agents that are active on human cells. A wide variety of assays may be used for this purpose, including immunoassays for protein binding; determination of cell growth, differentiation and functional activity; production of cytokines, e.g. IFN-γ, IL-2; and the like.

Also provided are reagents and kits thereof for practicing one or more of the above-described methods. The subject reagents and kits thereof may vary greatly. In certain embodiments, the kits include at least a PTK7 antibody. In other embodiments, the kit includes at least one antibody specific for a T cell marker, e.g. CD4, CD8, CD3, etc. The antibody may be labeled or the kit may provide reagents for labeling the antibody. In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are included to illustrate the invention and methods used in practicing the invention, and not to limit the invention.

EXAMPLES

Protein Tyrosine Kinase 7 is a Novel Marker for CD4+ T-Lineage Recent Thymic Emigrants Results CD4+CD8− thymocytes and cord blood CD4+ T cells express high levels of PTK7 mRNA. We reasoned that cord blood CD4+ T cells should be highly enriched in RTEs compared to circulating naïve CD4+ T cells of adults, an idea supported by the sjTREC content of these two cell populations (FIG. 1A). We hypothesized that RTEs, including those contained in cord blood CD4+ T cells, would have a subset of genes with an expression profile similar to that of mature CD4+CD8− thymocytes and distinct from the expression profile of adult naïve CD4+ T cells. Two pilot experiments using a small cDNA microarray of approximately 2500 targets were performed in which the transcript abundance of adult naïve CD4+ T cells was compared with either that of post-natal CD4+CD8− thymocytes or cord blood CD4+ T cells. Using real-time PCR, we confirmed that transcripts for PTK7 (FIG. 1B), a member of the receptor tyrosine kinase family and sox-4, a transcription factor involved in thymocyte development, were expressed at higher levels by cord blood CD4+ T cells and CD4+CD8−thymocytes compared to adult naïve CD4+ T cells. We subsequently focused on evaluating PTK7 as a marker for CD4+ RTEs, as this protein is expressed on the cell surface and would potentially be simpler to evaluate by immunofluorescent antibody staining and flow cytometry than a nuclear transcription factor.

Figure 2:
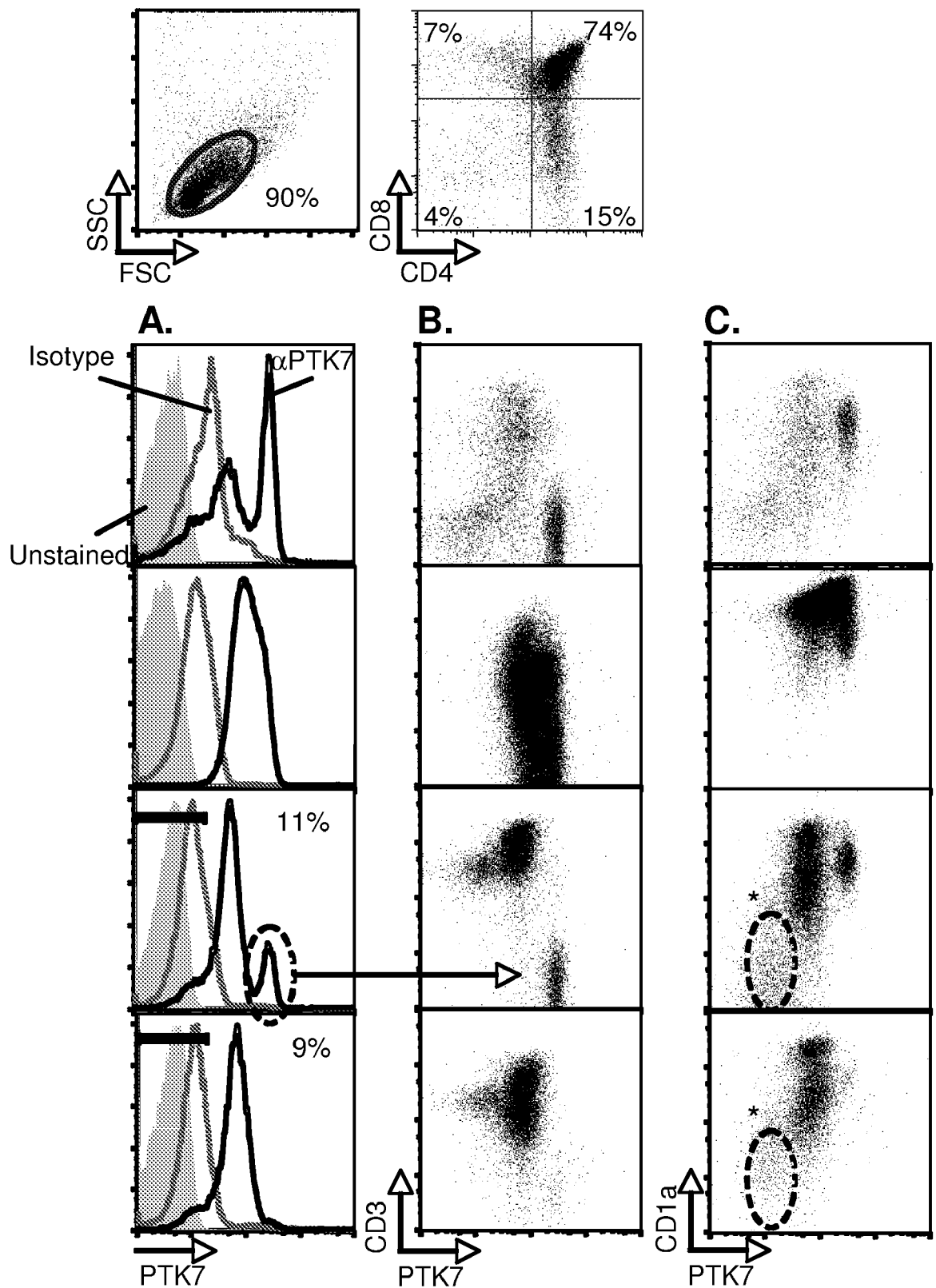
FIG. 2. PTK7 is expressed on human thymocytes. (Shaded region=unstained, dashed line=isotype-stained, solid line=anti-PTK7 stained cells.) (A). Expression is highest on the most immature cells (CD4−CD8− thymocytes), and decreases as the cells mature through the CD4+CD8+, and CD8+CD4− or CD8−CD4+ stages. (B). The maturation-specific expression level of PTK7 is further shown in the CD3 versus PTK7 dot plots. The PTK7$^{hi}$ expressing cells in the bimodal pattern of the CD4+CD8− population represents the immature single positive ("ISP") thymocytes that are CD3− and are a transitional population between CD4−CD8− and CD4+CD8+ thymocytes. (C). The CD1$^{low}$ thymocytes that are CD3$^{hi}$ are about to be exported to the periphery and retain PTK7 expression above the level in the isotype-stained control. The small percentage of PTK7−CD1− cells may be thymic re-entrants. The figures are a representative example of three experiments on different human thymi.

PTK7 is expressed on human thymocytes. To confirm the RNA expression findings at the protein level, we analyzed human thymocytes for surface expression of PTK7 in conjunction with CD4, CD8, CD3 and CD1a using a polyclonal PTK7 antibody (Lu et al. (2004) Nature 430:93-98. The least mature triple-negative (CD3−CD4−CD8−) subset of thymocytes (TN) showed the highest expression of PTK7 (FIG. 2 A). In contrast, CD4+CD8+ thymocytes, a more mature subset, had less expression, and most single-positive CD4+ CD8− and CD4−CD8+ thymocytes, which include the most mature cells, had the lowest level of expression. A minority of CD4+CD8− thymocytes had a level of PTK7 staining that was the same as TNs. These PTK7$^{high}$ CD4+CD8− thymocytes lacked expression of CD3 (FIG. 2 B), demonstrating that they constituted an immature single-positive thymocyte population that in humans is a transition between the triple-negative and CD4+CD8+ stages of thymocyte development. Thus, there was an inverse relationship between PTK7 surface expression and human thymocyte maturation.

We used CD1a staining to further define the relationship between PTK7 expression level and the maturation of single-positive thymocytes that had undergone positive selection. CD1a is a non-classical MHC class I molecule that is progressively lost from CD3$^{high}$ single-positive thymocytes as they mature. This is confirmed in the staining (FIG. 2 C), as the single positive cells with lowest PTK7 expression also express the lowest levels of CD1a. Interestingly, there is a population of cells that are PTK7−CD1− that may represent thymic re-entrants (they also show an intermediate level of CD3 expression FIG. 2 B).

Figure 9:
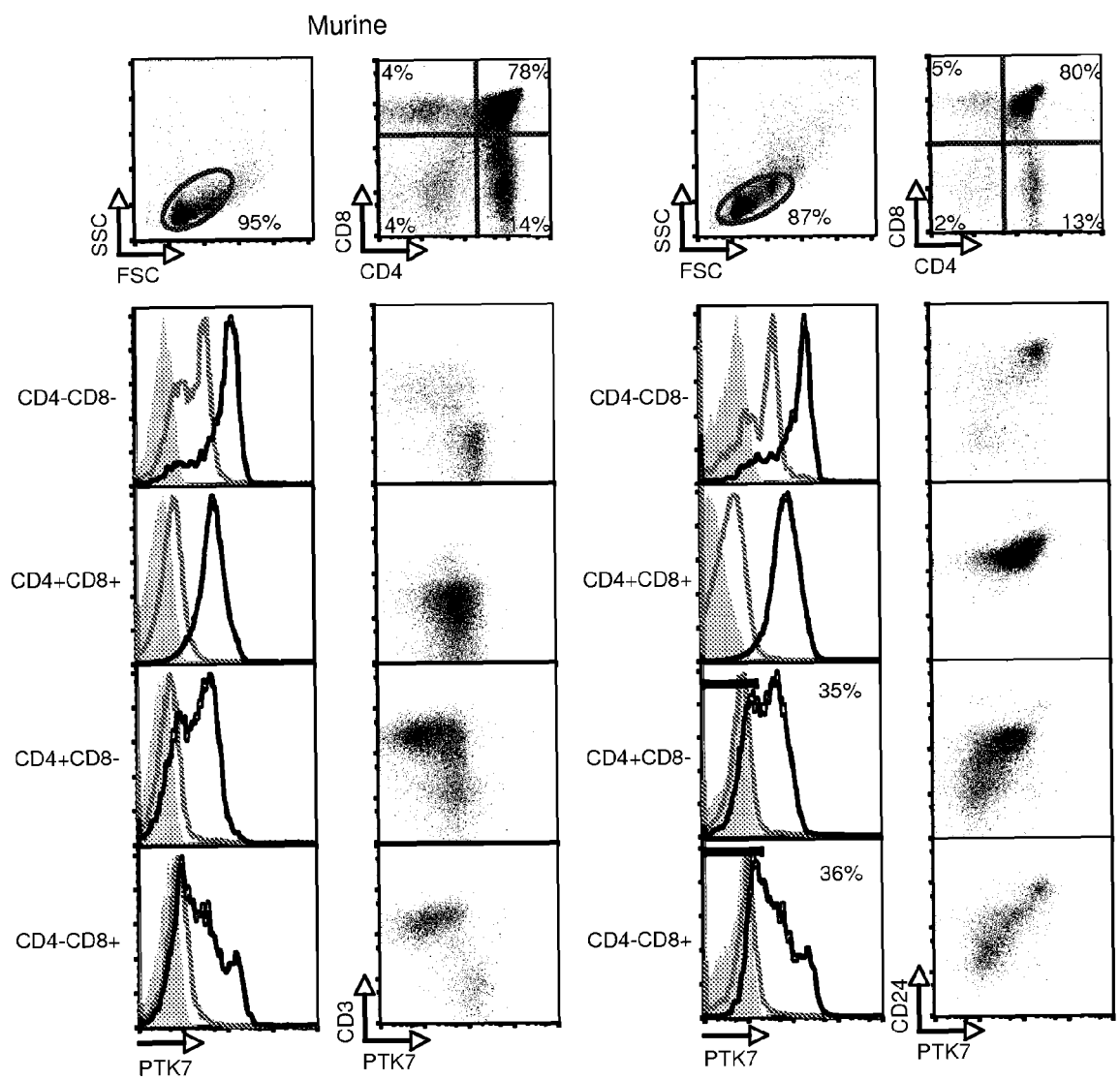
FIG. 9. PTK7 is expressed on murine thymocytes. (Light line in the histogram=unstained cells, gray line=isotype-stained cells, and black line=anti-PTK7 stained cells.) Expression is highest on the most immature cells (CD4–CD8– thymocytes), and decreases as the cells mature through the CD4+CD8+, and CD8+CD4– or CD8–CD4+ stages. The maturation-specific expression level of PTK7 is further shown in the plots with CD3 and CD24. The PTK7 expressing cells in the bimodal pattern the of CD8+CD4– plot represent the population of immature CD8+C4– single positive thymocytes which are CD24$^{high}$ and CD3$^{low}$ and are an intermediate between CD4–CD8– and CD4+CD8+ thymocytes in most mouse strains. These data are a representative example of four experiments on different mouse thymi.

Murine thymocytes, like those of the human, also showed a progressive decrease in PTK7 expression with maturation in several strains (C57BL/6, BALB/c, and FVB/N) (FIG. 9). Previous work has shown that in most mouse strains, CD3− CD4−CD8+ thymocytes are an intermediate cell population between the triple-negative and CD4+CD8+ thymocyte stages. Also, analogous to CD3+ single-positive human thymocyte maturation, CD4+CD8− single positives that had high levels of PTK7 expression were also CD24$^{high}$, indicating they were less mature and with reduced function compared to CD24$^{low}$ cells.

PTK7 is expressed on a small population of human adult peripheral naïve CD4+ T cells. Next, we wanted to determine whether any peripheral T cells maintained a level of expression of PTK7 after export from the thymus that would mark them as RTEs and distinguish them from older, more mature naïve T cells. As shown in FIG. 2A, approximately 10-15% of the FSC$^{lo}$SSC$^{lo}$ (lymphocyte) CD4+CD45RA$^{hi}$ cells showed expression of PTK7 at low levels. This small percentage of cells was consistently seen in 4 separate donors of varying ages (ages 24, 25, 30, and 37) and sexes (2 females, and 2 males) (FIG. 2B). The percentage of cells expressing PTK7 is consistent with murine models of RTEs that suggest there is a small amount of thymic output even in two-year old mice.

In the human, CD45RA is a tyrosine phosphatase isoform that marks naïve T cells, whereas memory T cells lose CD45RA expression and begin to express the shorter CD45RO isoform (Clement (1992) J Clin Immunol 12:1-10). The PTK7+ shoulder of cells was lost in the CD45RA$^{lo}$ population (FIG. 2A), again indicating the specificity of the staining. In stark contrast, the level of PTK7 expression was uniformly high on nearly all cord blood CD4+ T cells (FIG. 2A). Although not all cord blood CD4+ T cells are thought to be RTEs, this population is known to be enriched in RTEs. In addition, cord blood CD8+ T cells also showed lower, but still positive levels of PTK7 expression.

PTK7+ cells are wholly contained within the "younger" CD31+ population, and contain higher TREC levels than either PTK7−CD31+ or PTK7CD31− populations. To confirm that PTK7+ cells truly represent RTEs, we co-stained the same sets of cells for an additional maturation molecule, CD31, which has been previously characterized with regard to the relative age of peripheral T cells. The majority of naïve CD4+CD45RA$^{hi}$ T cells express CD31, which is also an endothelial cell marker (also called PECAM-1) that contains ITIM domains thought to inhibit TCR signaling. Sorted populations of CD31− T cells contain fewer TRECs than their naïve CD31+ counterparts, and by definition have undergone more cell divisions (Kimmig et al. (2002) J Exp Med 195: 789-794). Therefore, T cells that undergo homeostatic proliferation (independent of antigen, because they maintain their naiveté) in the periphery lose CD31 expression.

Figure 3:
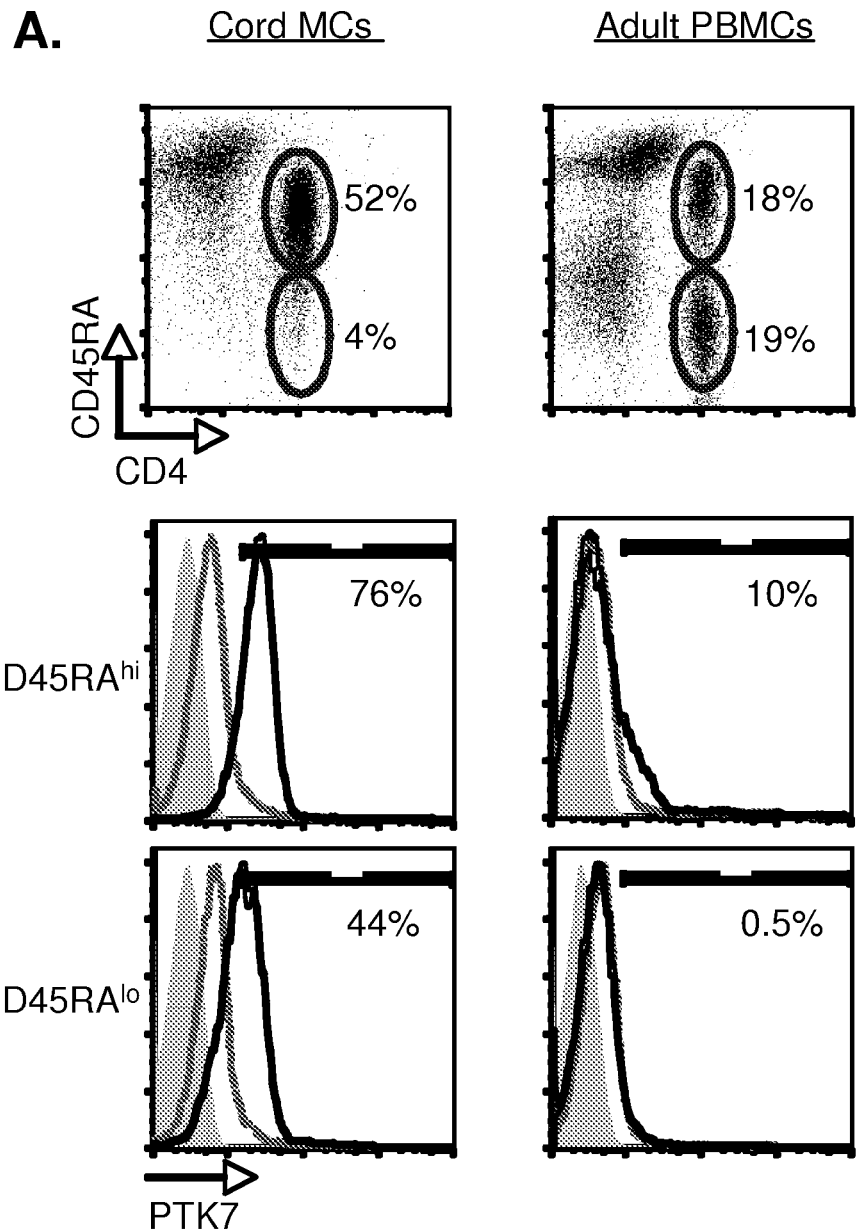
FIG. 3. PTK7 is expressed on a small population of human adult peripheral blood CD4+CD45RA$^{hi}$ naïve T cells and on the majority of neonatal cord blood CD4+ T cells. (Shaded region=unstained, dashed line=isotype-stained, solid line=anti-PTK7 stained cells.) (A). Cells shown in histograms are gated on lymphocytes (based on forward scatter (FSC) and side scatter (SSC)) and either CD4+CD45RA$^{hi}$ or CD4+CD45RA$^{lo}$ cells. The percentages shown in the histograms represent the anti-PTK7 specific staining % minus the isotype-stained % s (i.e., 16.2−6.2=10% for CD45RA$^{hi}$ cells, and 5.3%−4.8%=0.5% for the CD45RA$^{lo}$ cells. (B) A panel of % s of PTK7+ cells from a total of 3 umbilical cord blood samples (N=3) and 4 adult donors (N=4). Bars represent the mean of the donors, and the bars represent the standard deviation for the donors for the CD45RA$^{hi}$ and CD45RA$^{lo}$ populations, respectively.
Figure 3:
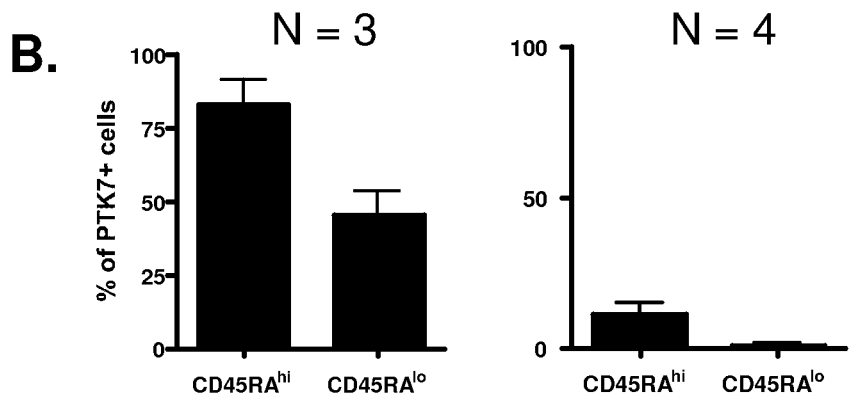

We hypothesized that the PTK7+ cells are RTEs, have undergone the fewest divisions in the periphery (having just emigrated from the thymus), and would be contained entirely within the younger CD31+ population, and not within the CD31− "older" population. We stained peripheral T cells from the same three donors shown in FIG. 2 and gated on lymphocyte CD4+CD45RA$^{hi}$ cells, followed by a two-dimensional analysis of PTK7 and CD31 staining. As shown in FIG. 3, all of the PTK7+ cells are also CD31+, and all the CD31− cells (that have undergone homeostatic proliferation) are also PTK7−, as expected. PTK7+ and PTK7− cells express similar levels of CD5, a marker whose expression level that is unaffected by the maturation state of the cell, and irrelevant isotype-matched stained cells are included as a negative control (FIG. 3A).

To confirm the validity of the staining, we sorted these three populations of cells (from the same three donors) based on PTK7 and CD31 co-staining, isolated total DNA from the cells, and performed an analysis for absolute TREC content, using a plasmid-based quantitative real-time PCR system on total DNA (Douek et al. (1998) *Nature* 396:690-695). TRECs have been used classically to determine the relative "age" of bulk populations of cells. They are the signal-joint circular remnants of VDJ recombination leftover after TCR gene rearrangement in the thymus. Because they lack an origin of replication, they are not replicated during each cell division, and as such are diluted in T cells following cell proliferation (Kong et al. (1998) *Immunity* 8:97-104). Unfractionated human thymocytes were used as the positive control and showed the highest TREC levels (FIG. 3B). The erythroleukemia cell line K562 was used as the negative control. The $PTK7^-CD31^+$ cells (population II) contain higher TREC levels than the $PTK7^-CD31^-$ cells (population III). RTEs should contain higher TREC content than older mature naive T cells since they have undergone fewer cell divisions (because of their recent thymic origin). Indeed, the level of TRECs in the $PTK7^+CD31^+$ cells (population II) is higher than the $PTK7^-CD31^+$ cells (population II). The absolute numbers from these data are consistent with numbers from Kimmig et al. (2002) *J Exp Med* 195:789-794. Additional controls for TREC content from unfractionated $CD45RA^+$ and $CD45RO^+$ populations were included to verify the expected results. Given that the majority of the $CD45RA^+$ population is the $CD31^+PTK7^-$ subset, it is expected that the number of TRECs from these two cell types would be most similar, and indeed they are (FIG. 3B). The relative "ages" of human $CD4^+$ T cells in the periphery can be delineated as 1. $PTK7^+$ $CD31^+$ (RTEs), which are the youngest peripheral $CD4^+$ T cells recently emigrated from the thymus, II. $PTK7^-CD31^+$ (non-RTEs) and III. $PTK7^-CD31^-$ (non RTEs).

Figure 4:
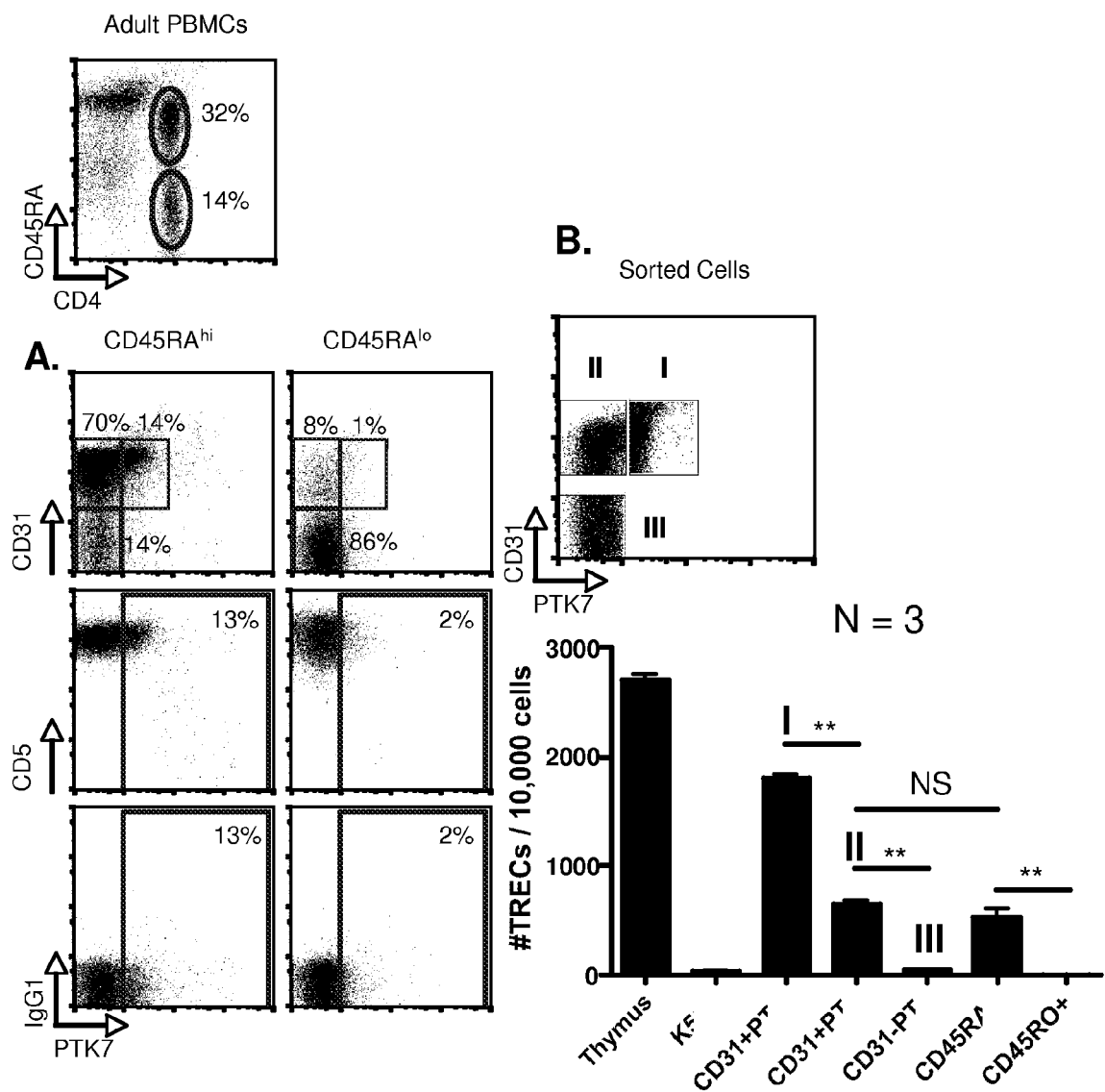
FIG. 4. PTK7+ T cells are recent thymic emigrants. (A). Either lymphocyte CD4+CD45RA$^{hi}$ cells or their CD45RA$^{lo}$ counterparts were gated as before, then co-analyzed for CD31 and PTK7 surface expression by flow cytometry after staining. All PTK7+ cells are also CD31+, indicating that the CD31− population, which has undergone homeostatic proliferation, does not contain any PTK7+ cells. Co-staining with CD5 and the an irrelevant IgG1 isotype control for the CD5 and CD31 antibodies verifies that PTK7 stain is uniform across a positively staining and a negatively staining population, where expression of the second marker is uniform and independent of the maturation state of the cell. These data are representative of six separate experiments with four different adult donors. (B). Cells were stained as previously described, and sorted into three separate populations (PTK7+CD31+=I, PTK7−CD31+=II, and PTK7−CD31−=III). Total DNA was isolated from the sorted cells and subjected to analysis for TCRα and sjTREC levels. Unfractionated infant human thymocytes and cord blood CD4+ T cells are the positive controls shown in the first two lanes, and K562 represents the negative control, an erythroleukemia cell line that contains no TRECs. Absolute #s of TREC levels were determined by correcting each sample for cell # based on TCRα levels. Bars represent the means of triplicates, and the error bars are standard deviation. This experiment was repeated three times for a single donor (age 36), and similar results were obtained for two separate donors (aged 25 and 31).

$CD4^+CD25^+FoxP3^+$ regulatory T cells do not express PTK7. To further confirm our finding about the relationship between PTK7 expression, TREC content, and peripheral age of a cell based on the number of cell divisions, we wanted to investigate the expression level of PTK7 on $CD4^+CD25^+$ $FoxP3^+$ regulatory T cells. It has been shown in previous reports that most regulatory T cells do not contain TRECs because they undergo homeostatic proliferation to self antigens in the periphery (Kasow et al. (2004) *J Immunol* 172: 6123-6128). We therefore hypothesized that PTK7 would not be expressed on any regulatory T cells in the periphery. This is, in fact, exactly what we found (FIG. 4). The permeabilization procedure did not destroy the PTK7 epitope, as there are still $PTK7^+$ cells remaining in the stain in the $Foxp3^-$ populations (FIG. 4). Therefore, the lack of coexpression of PTK7 and FoxP3 is similar to the lack of coexpression of PTK7 and CD31, since both populations have undergone homeostatic proliferation and contain lower TREC levels.

Figure 5:
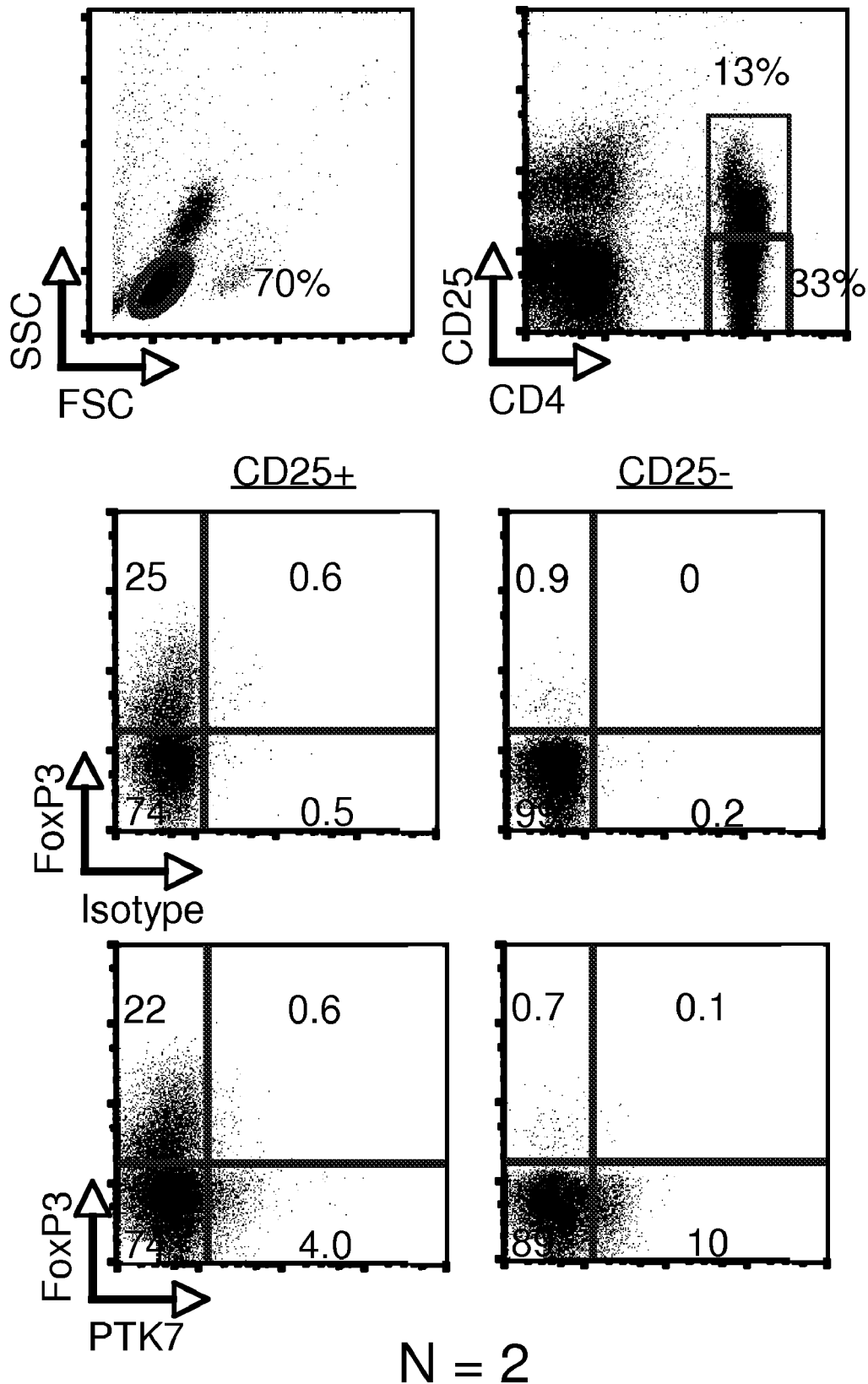
FIG. 5. CD4+CD25+FoxP3+ regulatory T cells, most of which have undergone homeostatic proliferation to self antigens in the periphery, no longer express PTK7. Cells were stained for CD4, CD25, and PTK7 as before, then fixed and permeabilized with an intracellular staining protocol for the FoxP3 transcription factor. The majority of the PTK7+ cells are in the CD25 gate and are FoxP3 negative, i.e., they are not regulatory T cells, although there are some CD25+FoxP3– cells. This is a representative experiment from two separate adult donors.

Functional characterization of human $CD4^+PTK7^+$ RTEs. We set out to determine whether adult $CD4^+$ RTEs differ in their functional ability as compared to $PTK7^-$ older mature naïve T cells. Previous studies in other species have suggested that CD4+ and CD8+ RTEs have immaturities in their immune function, including reduced proliferation and cytokine production in response to physiological TCR/CD3 stimuli (Boursalian et al. (2004) *Nat Immunol* 5:418-425). Human neonatal cord blood $CD4^+$ T cells, which have been classified as being enriched in RTEs, have also been shown to have immaturities in function (Chen et al. (2006) *Biol Blood Marrow Transplant* 12:160-171). As proliferation and cytokine production are the two main components representative of T-cell activation and differentiation, we sorted both PTK7+ and PTK7– cells from multiple donors as described previously, then placed them in culture with αCD3/28 beads for a 5-day time course. We measured $^3$H-Thy incorporation in the final 16 hours of culture. The PTK7+ cells showed a significant decreased ability to incorporate radiolabeled nucleotides (FIG. 5). Engagement of the PTK7 molecule by the antibody itself does not affect the proliferation of the cells, because cord blood cells proliferate to the same degree whether they are initially engaged by the antibody or not (FIG. 5).

Figure 6:
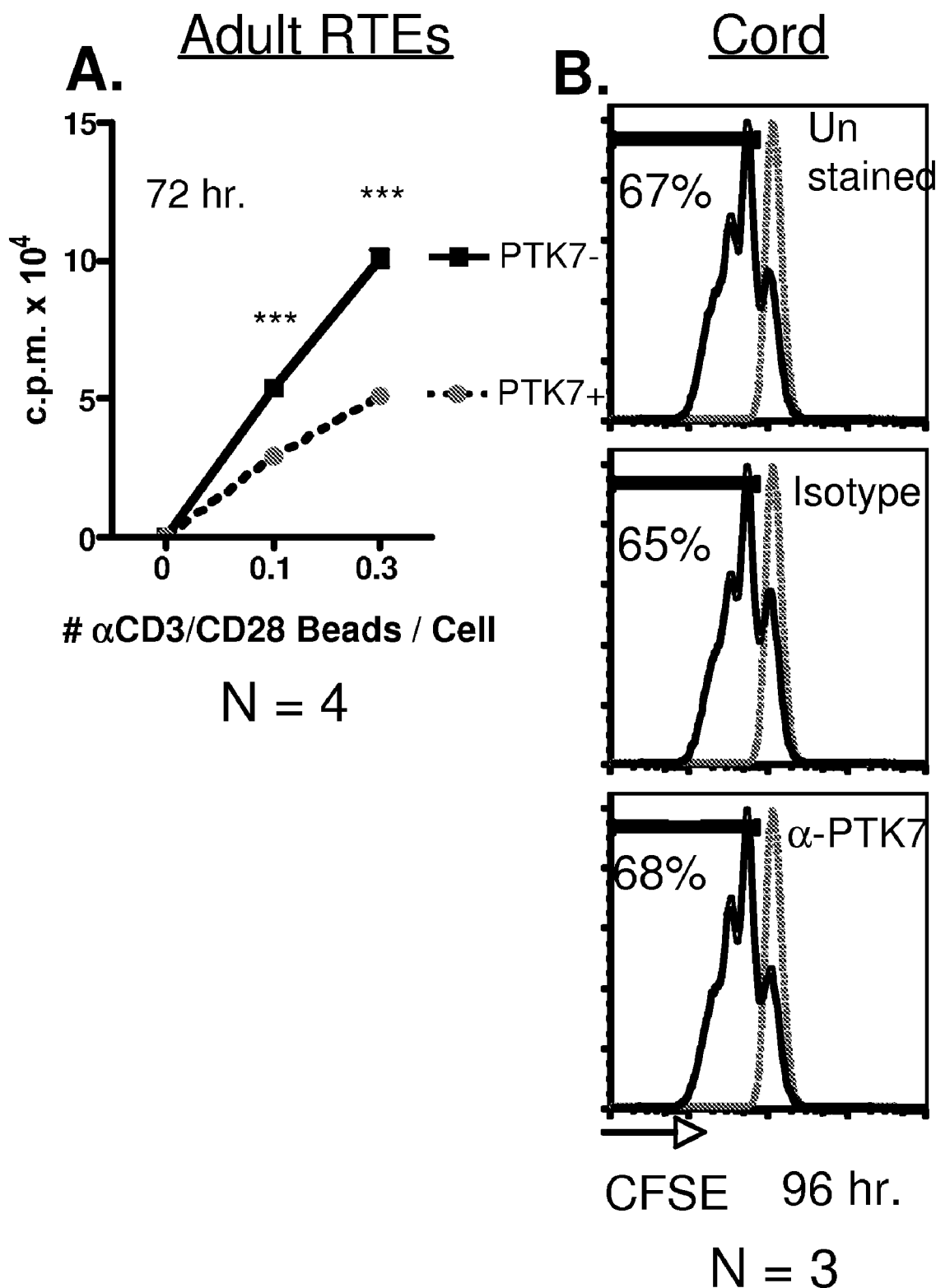
FIG. 6. PTK7+RTEs exhibit immaturities in immune function, including clonal expansion in response to a TCR/CD3 stimulus in vitro. (A). PTK7+ and PTK7' naïve T cells were sorted and placed in culture with anti-CD3/CD28 beads and stimulated for 72 and 96 hours. $^3$H-thymidine incorporation was assessed in the final 16 hours of culture. PTK7+ cells did not proliferate as well as PTK7– cells at all timepoints tested. (B). Simple binding of the anti-PTK7 antibody to endogenous PTK7 expressed on the cell surface does not impair the proliferative response of cord blood CD4+ purified T cells (a population that uniformly expresses relatively high levels of PTK7) to anti-CD3/CD28.

IL-7 is a homeostatic cytokine to which both thymocytes and cord blood T cells are responsive. Given that PTK7+ RTEs are of recent thymic origin, we hypothesized that they would be more responsive to IL-7 than their more mature counterparts. This was in fact what we observed (FIG. 6). Sorted cells from the same donors were incubated for 3 and 5 days with 10 ng/ml of recombinant human IL-7, and measured for $^3$H-thymidine incorporation for the final 16 hours of culture. The $PTK7^+$ cells were responsive, whereas the $PTK7^-$ cells were not. The counts per minute (CPM) were much lower than those for the TCR stimulated cells. We performed additional titration of the IL-7 to 50 ng/ml with similar results. We also carried the cells for 12 days in the presence of the IL-7, and only got an increase to about 4000 CPM. The difference in responsiveness to IL-7 was not due to differences in IL-7R-alpha expression, as both PTK7+RTEs and PTK7– mature $CD4^+$ T cells express comparable levels of IL-7R-alpha (FIG. 6).

Figure 7:
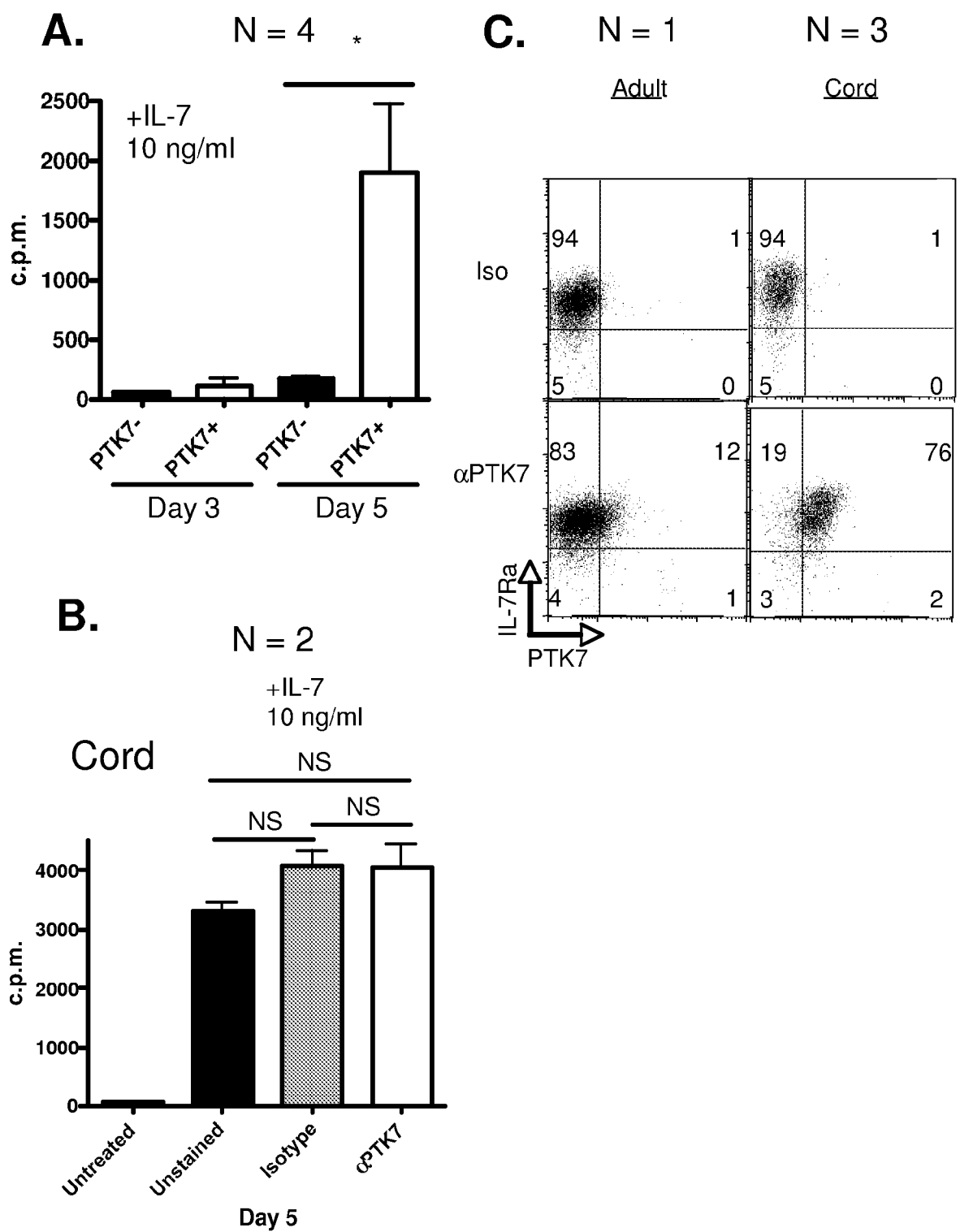
FIG. 7. PTK7+ RTEs retain thymocyte-like properties such as the ability to respond by proliferating to IL-7 in vitro. (A). PTK7+ and PTK7– sorted cells were placed in culture with 10 ng/ml recombinant hIL-7 for 5 days and assayed for $^3$H-thymidine incorporation in the final 16 hours of culture. (B). Simple binding of the anti-PTK7 antibody to endogenous PTK7 expressed on the cell surface does not alter the proliferative response of cord blood CD4+ purified T cells (a population that uniformly expresses relatively high levels of PTK7) to rhIL-7. (C). The lack of ability of PTK7– cells to respond to IL-7 is not due to an inability to express the IL-7R alpha chain.

To identify additional immaturities in function, we also investigated the ability of the cells to produce IL-2, TNF-α, and IFN-γ. Cells were sorted from the same donors as described before, and incubated with αCD3/CD28 beads for 12 hours, then permeabilized and stained for intracellular IL-2 and TNF-α. The $PTK7^+$ cells showed a dramatic reduction in the percentage of cells positive for IL-2 production (FIG. 7). This reduction was specific for IL-2, as the percentage of cells positive for TNF-α was similar for the two populations. The reduction in IL-2 production was mirrored in the level of IL-2 protein present in the supernatant, as measured at 12, 24, and 48 hours of culture (FIG. 7).

Figure 8:
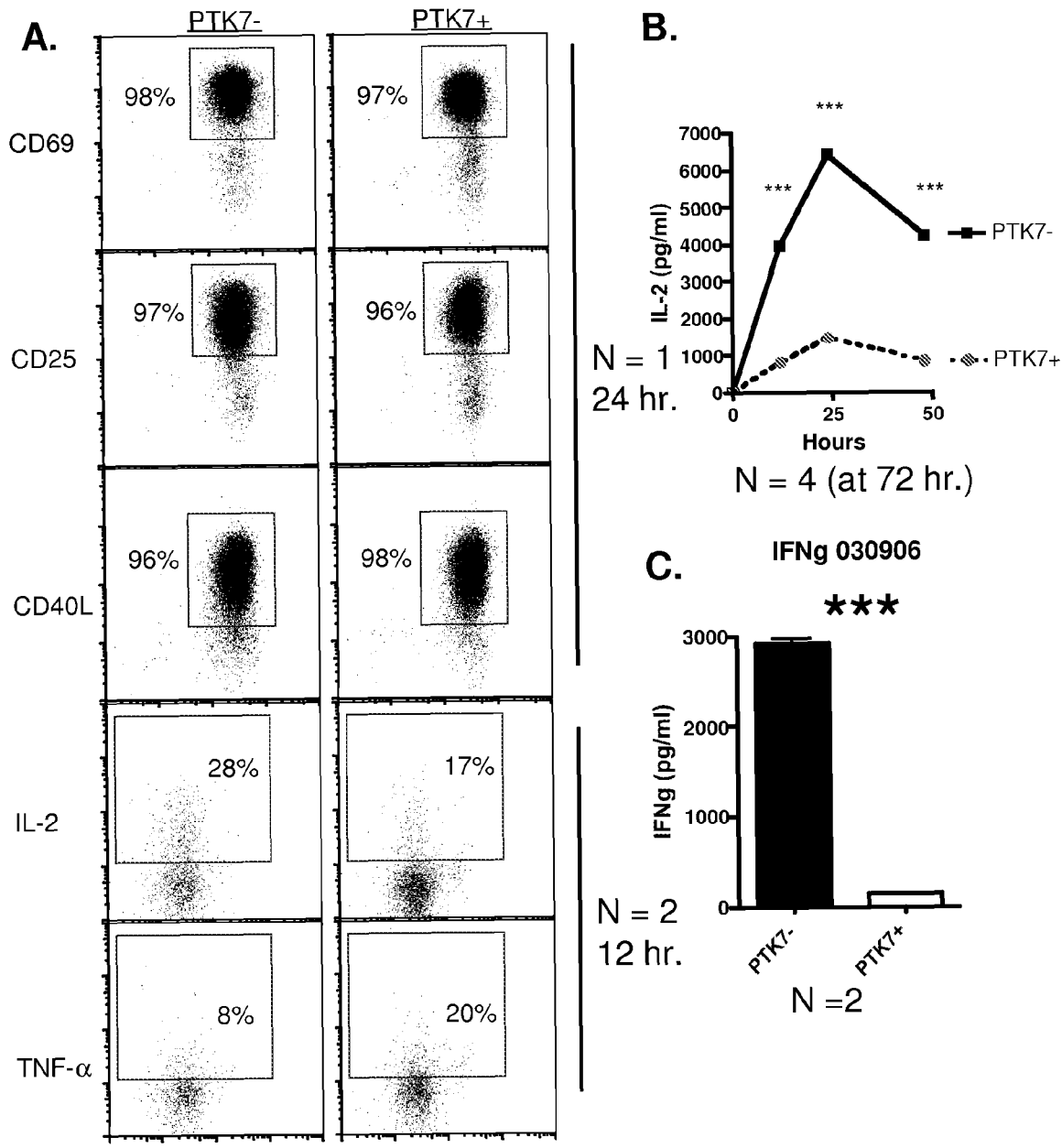
FIG. 8. PTK7+RTEs display immaturities in the ability to secrete IL-2 and the T helper 1 (Th1) signature cytokine interferon-gamma (IFN-γ). (A) PTK7+ and PTK7– naïve T cells were sorted and placed in culture with anti-CD3/CD28 beads and stimulated for 12 hours, followed by an intracellular cytokine stain. (B) Supernatants were collected and assayed by sandwich ELISA at the indicated timepoints. (C) For the IFN-γ, the sorted cells were co-incubated with autologous CD14+ MACS-purified monocytes and cultured for 3 days in the presence of anti-CD3/CD28 beads.

Infants are more susceptible to infectious diseases that require Th1 immunity, and neonatal T cells in the mouse and human have been shown to have reductions in the ability to produce the Th1 signature-cytokine, IFN-γ. Because neonatal T cells are enriched for RTEs, we predicted that adult PTK7+ RTEs would bear an immaturity in the production of IFN-γ. Because T cells require a period of time for differentiation into cytokine expressing cells and also require multiple interactions between T cells and antigen-presenting cells (APCs) for the induction of IFN-γ, we decided to include autologous MACS-purified $CD14^+$ cells at a ratio of 1:10 to the T cells in the bead-treated cultures as shown in FIG. 8. Following three days of culture, we collected supernatants and performed IFN-γ cytokine ELISAs. The $PTK7^+$ cells showed a drastic reduction in the ability to produce IFN-γ in response to TCR/CD3 stimuli in the presence of autologous $CD14^+$ monocytes. Materials and Methods.

Figure 10:
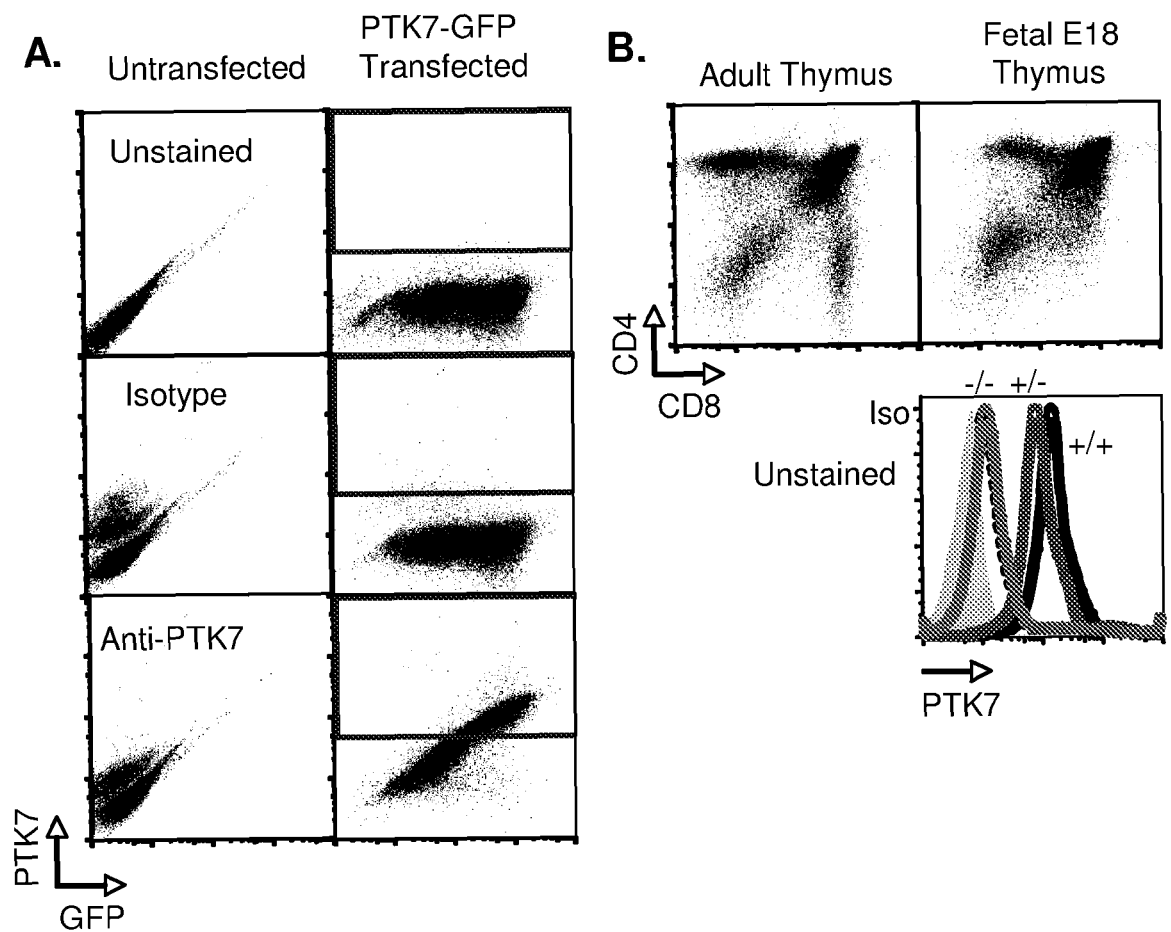
FIG. 10. PTK7 polyclonal anti-serum specifically binds a PTK7-GFP transfected cell line, and does not bind PTK7–/– murine thymocytes. (A) PTK7 polyclonal anti-serum specifically binds a PTK7-GFP transfected cell line. DNA sequence encompassing the extracellular and transmembrane regions of mouse PTK7 was cloned by RT-PCR from murine thymus RNA. It was then cloned into pEGFP-N3, which contains the CMV immediate early promoter and creates a GFP fusion protein, with eGFP at the C-terminus of the protein, and hence on the cytoplasmic side of the cell (PTK7 is a Type I transmembrane protein). CHO-P cells were then transfected by electroporation with pEGFP-N3-PTK7. The staining experiment was repeated once with similar results. (B) Anti-PTK7 does not bind to PTK7–/– murine thymocytes. Embryonic day 18 (E18) murine thymocytes from wild type (solid line), heterozygous (gray line), and knock-out (light gray line) embryos were stained with the anti-PTK7 serum. The intermediate staining of the heterozygous thymocytes likely indicates that PTK7 transcripts are normally generated from both homologous chromosomes. Unstained (shaded region), and Isotype-stained wild type thymocytes (dashed line) are also displayed as negative controls. CD4 and CD8 dot plots of adult and embryonic thymocytes are shown for comparison to indicate the lack of maturity of the E18 thymocytes. This experiment is a representative example from three separate experiments.
Figure 11:
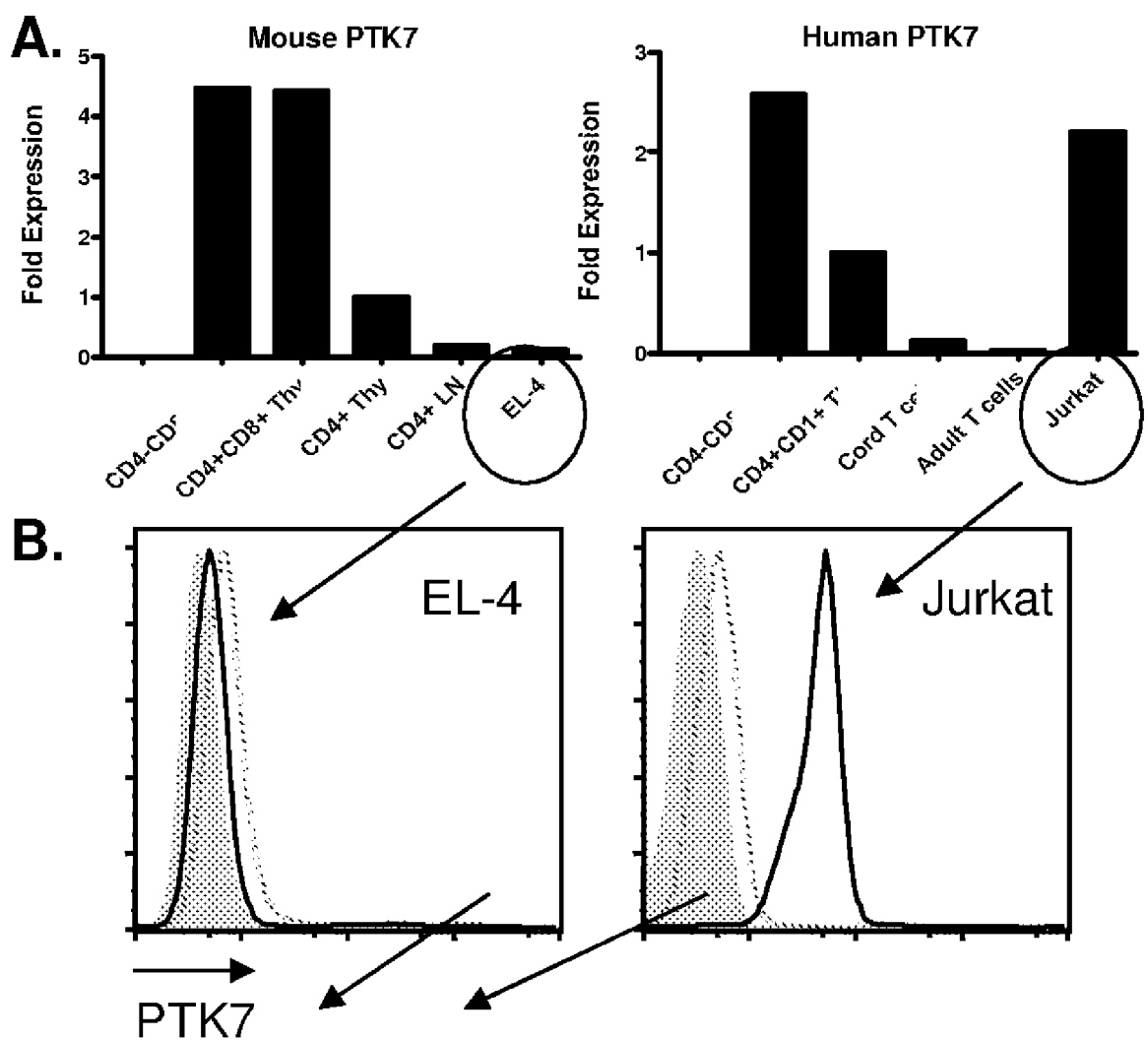
FIG. 11. The anti-mouse PTK7 anti-serum specifically recognizes both mouse and human PTK7 proteins in both native (flow cytometry) and denatured (western blot) protein states. A). Total RNA was extracted from both mouse and human thymocytes and peripheral T cells, and cell lines, and was reverse-transcribed into cDNA. Quantitative real-time PCR was performed with SyberGreen detection using primers to a C-terminal sequence of human PTK7, and an N-terminal sequence of mouse PTK7. B). Jurkat (human) and EL-4 (murine) cell lines were stained with the anti-PTK7 antiserum (shaded region=unstained, dashed line=isotype-stained, solid line=anti-PTK7 stained cells). The quantitative PCR graphs correspond directly to the flow cytometry profiles showing PTK7 protein expression specifically in Jurkat T cells and not EL-4 cells. The anti-PTK7 serum also binds denatured PTK7 protein in a western blot format. Total cell lysates from 1) EL-4 cell line, 2) Jurkat cell line, 3) mouse spleen, 4) recombinant PTK7, 5) mouse brain, and 6) mouse thymus.

Anti-PTK7 antibody. Additional control experiments were performed to verify the specificity of the anti-serum, including antibody binding to CHO cells transfected with a GFP-PTK7 fusion construct, lack of antibody binding to PTK7–/– murine fetal thymocytes, and additional expression analysis on mouse and human T cell populations using quantitative real-time PCR, flow cytometry, and western blotting (FIGS. 10 and 11).

Microarrays. Microarray experiments were performed as previously described by Alizadeh et al. (2000) *Nature* 403: 503-511.

Thymocyte staining. C57BL/6 murine thymus was ground with frosted slides (and human thymus from pediatric cardiac surgery patients was ground through a strainer) into a single-cell suspension, and filtered through a nylon mesh. $1.5 \times 10^6$ thymocytes were counted and aliquoted into 1.5 ml Eppendorf tubes with 50 μl of 1×PBS pH 7.4 (Gibco), 1% BSA, 0.1% Azide ("PBA"). All staining was performed at room temperature unless otherwise indicated. Cells were incubated for 20 minutes with anti-CD16/32 (1:25) (Fc block, Caltag) (or 10% human AB serum for human cells) for 5 minutes, then with either affinity-purified anti-mouse PTK7 anti-serum (1:500) or affinity-purified Normal Rabbit IgG (1:50) (Caltag) as an isotype negative control. Cells were then washed in 1 ml of PBA, and stained for another 20 minutes with goat anti-rabbit IgG-FITC (H&L) (1:25) (Caltag). Cells were washed again, and then stained for 15 minutes at 4 degrees in Normal Rabbit IgG (1:20). Cells were washed again and then stained for 10 minutes with anti-CD8, anti-CD4, and anti-CD3. After a final wash, the cells were fixed with 2% para-formaldehyde in 1×PBS pH 7.4 and analyzed by flow cytometry on a FACScan or FACSCalibur. CD24-PE from BD Biosciences (clone Ml/69). Human CD1α-PE from BD Biosciences.

Human T-cell staining. PBMC were purified from either human umbilical cord blood samples (obtained from El Camino Hospital on scheduled C-sections) or peripheral blood of a 35-year-old male adult donor by Ficoll Hypaque density gradient purification. Whole blood was first mixed in a 50:50 ratio with 0.9% NaCl, then underlaid with Ficoll Hypaque and centrifuged. Interphase harvested cells were then washed twice with 1×HBSS, counted, and 1.5 million cells were stained and analyzed as previously described for thymocytes, using antibodies to human CD4 and CD45RA. Anti-human CD31-PE was obtained from BD Biosciences.

TREC Analysis. Freshly isolated human peripheral blood cells were prepared, stained, and sorted. Following the sort, cells were washed once with 1×PBS pH 7.4 (Gibco), then total DNA was prepared using a QIAamp DNA Mini Kit (Qiagen 51304). DNA was then frozen at −20° C. until use in real time PCR assays. For the real time PCR assays, a master mix was prepared using Taqman Universal PCR Master Mix (Roche 4304437), 10 μM forward primer 5'-CCATGCTGA-CACCTCTGGTT-3' (SEQ ID NO 1), 10 μM reverse primer 5'-TCGTCAGAACGGTGAATGAAG-3' (SEQ ID NO 2, and 10 μM probe FAM-TAMRA 5'-CACGGTGATGCAT-AGGCACCTGC-3' (SEQ ID NO 3).

An equal volume of total DNA from all samples was aliquoted into the master mix, then plated in triplicate. Plates were analyzed on the real time machine at 50° C. for 2', 95° C. for 10', then 50 cycles. A standard linear plot was generated with 10-fold dilutions of a cloned sjTREC starting with 100,000 copies and diluted to 10 copies. Parallel reactions were used for a cloned portion of TCRα, with 10.0 μM forward primer 5'-CCTGATCCTCTTGTCCCACAG-3' (SEQ ID NO 4), 10.0 μM reverse primer 5'-GGATTTAGAGTCTCT-CAGCTGGTACA-3' (SEQ ID NO 4), and 10.0 μM probe FAM-TAMRA 5'-ATCCAGAACCCTGACCCTGCCG-3' (SEQ ID NO 5). Values for the linear plot were either included or excluded to get an R squared value as close to 0.99 as possible, demonstrating an efficiency of amplification of close to 100%, and thus a Ct difference of 1 representing a 3 fold difference in copy number. For the calculations, the Ct value for each sample was interpolated by the machine based on this R squared value to get an absolute copy number. The calculation for absolute TREC # was determined with the following formula: # TCR alpha copies/2=# cells; # sjTREC copies/# cells=# sjTREC copies/cell. Then, the triplicates were averaged and standard deviation was performed using Graphpad Prism software. Finally, statistical comparisons between groups were performed using Prism software with unpaired student's T test to determine P values.

The standard TCRα (T cell receptor alpha constant region) fragment and the sjTREC fragment were both cloned by PCR from a preparation of unfractionated human thymocyte DNA into the TOPO vector. We cloned a 496 bp fragment of TCR alpha constant region from with 2 primers flanking the DNA sequences used as primers in the quantitative PCR assay described above. Primers are 5'-ATCACGAGCAGCTG-GTTTCT-3' (SEQ ID NO 7), and 5'-CCATTCCTGAAG-CAAGGAAA-3' (SEQ ID NO 8). The 381 bp fragment of sjTREC was cloned with the following 2 primers: 5'-GAAAACAGCCTTTGGGACAC-3' (SEQ ID NO 9), and 5'-GTGACATGGAGGGCTGAACT-3' (SEQ ID NO 10). Copy number was calculated using a combination of the OD reading and length of plasmid product.

In FIG. 5, the cells were prepared and stained as described previously. Then cells were fixed, permeabilized, and stained, and analyzed within 24 hours on a FACScalibur flow cytometer.

In FIG. 6: Freshly isolated human peripheral blood cells were prepared, stained, and sorted. Following the sort, cells were centrifuged and resuspended in RPMI (Gibco), 10% human AB serum, Pen/Strep/L-Glutamine. Cells were plated into 96 well round bottom plates in a final volume of 200 μl per well at a final concentration of 25,000 cells per well. Our own beads or Dynal beads (anti-CD3/anti-CD28) were added at a final concentration of 0.3 beads or 0.1 beads per cell. IL-7 was used at a final concentration of 10 ng/ml (from R&D systems). The IL-7 alone experiments used 50,000 cells per well. $^3$H-Thymidine was added on the final 18 hours of culture (1.0 μl per well) prior to harvesting on Day 2, 3, or 4.

CD14+ cells were added to ConA treated wells and to anti-CD3/anti-CD28 bead-treated wells at a concentration of 1:10 that of sorted T cells. Supernatants were collected on Day 3 of culture, frozen at −80 until, and IL-2, IFNγ were assayed by ELISA (BD optEIA).

FIG. 9. Total RNA from thymocytes of a 6-week old male wild type C57BL/6 mouse was extracted using Tri-reagent (MRC). RNA was treated with DNase I using an Absolutely RNA Nanoprep kit column (Stratagene). A cDNA library was then generated with random hexamer priming and Superscript II RNaseH- (Invitrogen). Mouse PTK7 116-2632 was cloned by PCR using PFU Turbo DNA polymerase (Stratagene) and the following primers (IDT): (Forward) 5'GGAATTCAGCCACCATGGGAGCCCGCCCGCTG-3' (SEQ ID NO 11), and (Reverse) 5'-TCCCCGCGGACTTC-CCGAACATCTCCACC-3' (SEQ ID NO 12).

The mouse PTK7 methionine start codon begins with nucleotide 116 and 2632 extends beyond the end of the transmembrane domain portion of the gene, which ends at nucleotide 2270. The forward primer above contains an EcoRI site at the 5' end, followed by the Kozak consensus translation start site ribosome binding site sequence GCCACC (SEQ ID NO 13) immediately 5' of the 116 PTK7 start codon. The reverse primer contains a Sac II site immediately 3' of the 2632 region of mPTK7. The restriction sites inserted during the PCR allowed for directional cloning of this segment of mPTK7 in frame into the multi-cloning site of pEGFP-N3, originally from Clontech (Catalog number 6080-1, Genbank accession # U57609). The construct was sequenced (Bionexus) to confirm 100% nucleotide identity throughout the designated length of the clone. It was then purified with the Endofree Plasmid Maxi kit (Qiagen), and digested to verify the ligation. Then, $10^6$ CHO-P cells were transfected by electroporation with 20 μg pEGFP-N3-PTK7. Briefly, cells were trypsinized, washed in complete medium, then once in 1×PBS, resuspended in 200 μl DMEM and placed on ice. Time constant was 50.6 and Actual Volts was 0.260. Cells were allowed to recover for 20 minutes on ice prior to plating in complete medium. Cells were grown for 3 days and analyzed by flow cytometry to verify GFP fluorescence. Cells were then selected for 2 weeks with 1.0 mg/ml G418 in medium, changing the media daily. Following two weeks of selection in G418 to generate the stable transfectant, the cells were sorted based on GFP fluorescence and prepared and stained as previously described.

Timed matings were set up between pairs of PTK7$^{+/-}$ mice. To identify heterozygous mice, a small section of tail was removed with scissors. (All animals were cared for by the rules and regulations of Stanford Animal standard protocol). Then, tail sections were incubated with 100 µl of the following solution: 5.0 mM potassium ferricyanide, 5.0 mM potassium ferrocyanide, 2.0 mM magnesium chloride, 2.5 mg/ml beta-galactosidase (X-gal), 0.01% sodium deoxycholate, 0.02% NP-40, in 1×PBS pH 7.4. Tail sections were incubated for 1 hr in a 37° C. water bath and genotyped for blue (transgenic) or non-blue (wild-type) appearance. On Day 18 following impregnation, the mother mouse was sacrificed by cervical dislocation. Embryos were extracted, and their fetal thymi were removed under a dissection microscope. PTK7$^{-/-}$ embryos were easily identified by the neural tube defect. Heterozygous and wild type embryos were distinguished by the X-gal staining method described above using embryo tail sections. Thymi were then prepared and thymocytes were stained as previously described.

FIG. 11. Abbreviations: Mouse: NTC=no-template control, CD4−CD8− Thy=double negative thymocytes, CD8+CD4+ Thy=double positive thymocytes, CD4+Thy=CD8−CD4+ single positive thymocytes, CD4+ LN=CD8−CD4+ peripheral T cells from lymph node (LN), and EL-4=mouse CD4+ thymoma cell line. Human: CD4+CD1+ Thy=CD8−CD4+CD1+ single positive thymocytes, Cord T cells=unfractionated umbilical cord blood peripheral T cells, Adult T cells=unfractionated adult blood peripheral T cells, and Jurkat=CD4+ lymphoma cell line.

Primers (IDT) for the quantitative PCR reactions are as follows: Human PTK7 (Exon 4 618-808) (Forward) 620-639: 5'-CCACCTACCAATGGTTCCGA-3' (SEQ ID NO 14); (Reverse) 650-670: 5'-TGCTCTGACCATCAGAAAGGG-3' (SEQ ID NO 15). Mouse PTK7 (Exon 20 3141-4054). (Forward) 3427-2446: 5'-CAGGCATTGCTGAAGACTGG-3' (SEQ ID NO 16). (Reverse) 3458-3477: 5'-GGTTGTGGC-GAAGAGAAACG-3' (SEQ ID NO 17).

Lysates were prepared from single-cell suspensions of the indicated cell lines or mouse cell lines. Lysis buffer contained 1% NP-40, 50 mM Tris-HCl pH 7.5, 1 mM EDTA, and 250 mM NaCl. One tablet of "Complete Mini" protease inhibitors (Roche) was added per 5 ml lysis buffer. For mouse tissues, 5.0 million cells were used per 100 µl of lysis buffer, and for cell lines, 1.0 million cells were used per 100 µl. (Recombinant PTK7 was a gift from X. Lu). Cells were washed once in 1×PBS prior to lysis. After addition of lysis buffer, cells were vortexed and lysed on ice for 20' prior to centrifuging 20' max speed at 4° C. 1 µl of lysate in 100 µl of assay buffer in a Bradford assay was performed to determine the absolute protein concentration. Then 20 µg of total protein per sample was added to sample buffer, boiled, and loaded onto a 10% SDS-PAGE gel, blotted, blocked, and probed with the anti-PTK7 antibody. Goat anti-rabbit-HRP (Jackson) and ECL (KPL) were used for development.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. No reference to a publication herein should be construed as an admission that such is prior art.

---

What is claimed is:

1. A method of identifying a human naive T-cell, said method comprising determining the level of expression of PTK7 on a human T-cell.

2. The method of claim 1, wherein the T cell is in a peripheral blood or lymphoid tissue sample.

3. The method of claim 1, wherein the PTK7$^+$ cell is identified by contacting the T cell with fluorescently-labeled monoclonal antibodies which specifically bind to PTK7 and detecting the fluorescence of the labeled antibodies bound to the cell.

4. The method of claim 1, wherein the T cell is a CD4$^+$ cell.

5. The method of claim 1, wherein the T cell is a recent thymic emigrant.

6. A method of making an isolated population of human naive T cells, said method comprising obtaining a T-cell sample;
   determining the level of expression of PTK7 on the surface of the T cell; and
   isolating the PTK7$^+$ T cells from those T cells that are PTK7$^-$.

7. The method of claim 6, wherein the biological sample is contacted with a labeled monoclonal PTK7 antibody, and the cells are sorted according to the amount of the labeled antibody bound to them, wherein cells having bound antibody are identified as PTK7$^+$ cells and are isolated from cells lacking antibody bound to them.

8. A method of analyzing a human patient sample for the presence of naïve T cells, the method comprising:
   quantitating the presence of PTK7 protein or mRNA in a test sample, from a patient selected from an individual underdoing immunosuppressive treatment; an individual underdoing immune restoration treatment and an individual suffering from severe combined immunodeficiency, wherein the presence of PTK7 as compared to a control sample lacking naïve T cells is indicative of the presence of naïve T cells in the test sample.

9. The method of claim 8, wherein the sample is selected from peripheral blood, lymph node, spleen and cord blood.

10. The method of claim 9, wherein the sample is dried blood.

11. The method of claim 8, wherein the test sample is peripheral blood dried on paper.

* * * * *